(12) United States Patent
Baltezor et al.

(10) Patent No.: US 10,993,927 B2
(45) Date of Patent: *May 4, 2021

(54) TAXANE PARTICLES AND THEIR USE

(71) Applicant: CRITITECH, INC., Lawrence, KS (US)

(72) Inventors: Michael Baltezor, Lawrence, KS (US); Joseph Farthing, Lawrence, KS (US); Jake Sittenauer, Lawrence, KS (US); Jahna Espinosa, Lawrence, KS (US); Samuel Campbell, Lawrence, KS (US); Matthew McClorey, Lawrence, KS (US); Julia K. Fischer, Lawrence, KS (US); Mark D. Williams, Lawrence, KS (US); Gary E. Clapp, Lawrence, KS (US)

(73) Assignee: Crititech, Inc., Lawrence, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 17/023,635

(22) Filed: Sep. 17, 2020

(65) Prior Publication Data
US 2021/0000786 A1 Jan. 7, 2021

Related U.S. Application Data

(60) Continuation of application No. 16/669,310, filed on Oct. 30, 2019, which is a continuation of application
(Continued)

(51) Int. Cl.
A61K 31/337 (2006.01)
A61K 9/00 (2006.01)
(Continued)

(52) U.S. Cl.
CPC .............. *A61K 31/337* (2013.01); *A61J 3/02* (2013.01); *A61K 9/0019* (2013.01); *A61K 9/10* (2013.01);
(Continued)

(58) Field of Classification Search
None
See application file for complete search history.

(56) References Cited

U.S. PATENT DOCUMENTS

| 5,399,363 A | 3/1995 | Liversidge et al. |
| 5,626,862 A | 5/1997 | Brem et al. |

(Continued)

FOREIGN PATENT DOCUMENTS

| CN | 1463969 | 12/2003 |
| CN | 1923189 | 3/2007 |

(Continued)

OTHER PUBLICATIONS

Saloustros, et al. "Paclitaxel and docetaxel in the treatment of breast cancer." Expert opinion on pharmacotherapy 9.15 (2008): 2603-2616. (Year: 2008).*

(Continued)

*Primary Examiner* — Aradhana Sasan
(74) *Attorney, Agent, or Firm* — McDonnell Boehnen Hulbert & Berghoff LLP

(57) ABSTRACT

Compositions are provided that include having at least 95% by weight of a taxane, or a pharmaceutically acceptable salt thereof, where the particles have a mean bulk density between about 0.050 g/cm$^3$ and about 0.15 g/cm$^3$, and/or a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g. Methods for making and using such compositions are also provided.

18 Claims, 7 Drawing Sheets

Related U.S. Application Data

No. 15/895,197, filed on Feb. 13, 2018, now Pat. No. 10,507,195, which is a continuation of application No. 15/499,397, filed on Apr. 27, 2017, now Pat. No. 9,918,957, which is a continuation of application No. 15/261,108, filed on Sep. 9, 2016, now abandoned, which is a division of application No. 15/174,505, filed on Jun. 6, 2016, now Pat. No. 9,814,685.

(60) Provisional application No. 62/171,060, filed on Jun. 4, 2015, provisional application No. 62/171,001, filed on Jun. 4, 2015, provisional application No. 62/171,008, filed on Jun. 4, 2015.

(51) Int. Cl.

| | | |
|---|---|---|
| *A61K 9/10* | (2006.01) | |
| *A61K 9/14* | (2006.01) | |
| *A61K 9/16* | (2006.01) | |
| *A61K 9/51* | (2006.01) | |
| *A61J 3/02* | (2006.01) | |
| *B01J 19/10* | (2006.01) | |
| *B01J 19/26* | (2006.01) | |
| *B01J 2/04* | (2006.01) | |
| *B01J 3/00* | (2006.01) | |
| *B01J 4/00* | (2006.01) | |
| *B01D 46/24* | (2006.01) | |
| *B01J 3/02* | (2006.01) | |
| *B05B 1/34* | (2006.01) | |
| *B05B 13/02* | (2006.01) | |

(52) U.S. Cl.
CPC .............. *A61K 9/14* (2013.01); *A61K 9/1605* (2013.01); *A61K 9/1682* (2013.01); *A61K 9/1688* (2013.01); *A61K 9/5192* (2013.01); *B01D 46/24* (2013.01); *B01J 2/04* (2013.01); *B01J 3/008* (2013.01); *B01J 3/02* (2013.01); *B01J 4/002* (2013.01); *B01J 19/10* (2013.01); *B01J 19/26* (2013.01); *B05B 1/3489* (2013.01); *B05B 13/0278* (2013.01); *B01D 2271/02* (2013.01); *B05D 2401/90* (2013.01)

(56) References Cited

U.S. PATENT DOCUMENTS

| | | | |
|---|---|---|---|
| 5,833,891 A | 11/1998 | Subramaniam et al. | |
| 5,874,029 A | 2/1999 | Subramaniam et al. | |
| 5,874,481 A | 2/1999 | Weers et al. | |
| 5,886,026 A | 3/1999 | Hunter et al. | |
| 6,063,138 A | 5/2000 | Hanna et al. | |
| 6,113,795 A | 9/2000 | Subramaniam et al. | |
| 6,117,949 A | 9/2000 | Rathi et al. | |
| 6,221,153 B1 | 4/2001 | Castor et al. | |
| 6,348,209 B2 | 2/2002 | Placke et al. | |
| 6,419,901 B2 | 7/2002 | Placke et al. | |
| 6,562,952 B1 | 5/2003 | Rajewski et al. | |
| 6,616,849 B1 | 9/2003 | Osajima et al. | |
| 6,620,351 B2 | 9/2003 | Gupta et al. | |
| 6,689,803 B2 | 2/2004 | Hunter | |
| 6,749,868 B1 | 6/2004 | Desai et al. | |
| 6,811,767 B1 | 11/2004 | Bosch et al. | |
| 7,179,495 B1 | 2/2007 | Jan et al. | |
| 7,208,106 B2 | 4/2007 | Shekunov et al. | |
| 7,217,735 B1 | 5/2007 | Au et al. | |
| 7,276,190 B2 | 10/2007 | Reverchon | |
| RE40,493 E | 9/2008 | Straub et al. | |
| 7,455,797 B2 | 11/2008 | Shekunov et al. | |
| 7,556,798 B2 | 7/2009 | Edwards et al. | |
| 7,566,436 B2 | 7/2009 | Lester et al. | |
| 7,744,923 B2 | 6/2010 | Rajewski et al. | |
| 7,754,777 B2 | 7/2010 | Ventosa et al. | |
| 7,820,788 B2 | 10/2010 | Desai et al. | |
| 7,829,598 B2 | 11/2010 | Iversen et al. | |
| 7,833,444 B2 | 11/2010 | Watano | |
| 8,043,631 B2 | 10/2011 | Au et al. | |
| 8,138,229 B2 | 3/2012 | Desai et al. | |
| 8,221,779 B2 | 7/2012 | Jonas et al. | |
| 8,314,156 B2 | 11/2012 | Desai et al. | |
| 8,735,394 B2 | 5/2014 | Desai et al. | |
| 8,778,181 B1 | 7/2014 | Johnson et al. | |
| 8,906,392 B2 | 12/2014 | Berkland et al. | |
| 9,233,348 B2 | 1/2016 | Johnson et al. | |
| 9,278,069 B2 | 3/2016 | Berkland et al. | |
| 9,301,926 B2 | 4/2016 | Indolfi et al. | |
| 9,339,554 B2 | 5/2016 | Rijcken et al. | |
| 9,511,046 B2 | 12/2016 | Desai et al. | |
| 9,617,338 B1 | 4/2017 | Campbell et al. | |
| 9,763,946 B2 | 9/2017 | Lin | |
| 9,814,685 B2 | 11/2017 | Baltezor et al. | |
| 9,895,197 B2 | 2/2018 | Poquet et al. | |
| 9,918,957 B2 | 3/2018 | Baltezor et al. | |
| 2004/0033267 A1 | 2/2004 | Merisko-Liversidge et al. | |
| 2004/0092577 A1 | 5/2004 | Lerner et al. | |
| 2004/0220081 A1 | 11/2004 | Kreitz et al. | |
| 2005/0059613 A1 | 3/2005 | Memarzadeh et al. | |
| 2005/0131057 A1 | 6/2005 | Uneo et al. | |
| 2005/0238725 A1 | 10/2005 | Cunningham et al. | |
| 2006/0034925 A1 | 2/2006 | Au | |
| 2006/0078619 A1 | 4/2006 | Woo et al. | |
| 2006/0127420 A1 | 6/2006 | Chung et al. | |
| 2006/0147535 A1 | 7/2006 | Muthukumaran et al. | |
| 2006/0188566 A1 | 8/2006 | Liversidge et al. | |
| 2008/0063699 A1 | 3/2008 | Teifel et al. | |
| 2008/0089944 A1 | 4/2008 | Rajewski et al. | |
| 2008/0160095 A1 | 7/2008 | Desai et al. | |
| 2009/0215882 A1 | 8/2009 | Bouzada et al. | |
| 2010/0197944 A1 | 8/2010 | Palle et al. | |
| 2011/0223203 A1 | 9/2011 | Berkland et al. | |
| 2011/0293672 A1 | 12/2011 | Lewis et al. | |
| 2012/0087984 A1 | 4/2012 | Liversidge et al. | |
| 2012/0177910 A1 | 7/2012 | Weber et al. | |
| 2012/0237768 A1 | 9/2012 | Hirokawa et al. | |
| 2012/0321698 A1 | 12/2012 | Narain et al. | |
| 2014/0038931 A1 | 2/2014 | Hirokawa et al. | |
| 2014/0079782 A1 | 3/2014 | York et al. | |
| 2014/0154269 A1 | 6/2014 | Tour et al. | |
| 2014/0199244 A1 | 6/2014 | Rijcken et al. | |
| 2014/0294967 A1 | 10/2014 | Borbely et al. | |
| 2015/0037252 A1 | 2/2015 | Hawkett et al. | |
| 2015/0118311 A1 | 4/2015 | Zhou et al. | |
| 2015/0342872 A1 | 12/2015 | Williamson et al. | |
| 2015/0375153 A1 | 12/2015 | Johnson et al. | |
| 2016/0263232 A1 | 9/2016 | Amighi et al. | |
| 2016/0354336 A1 | 12/2016 | Baltezor et al. | |
| 2016/0374953 A1 | 12/2016 | Baltezor et al. | |
| 2017/0119881 A1 | 5/2017 | Saha et al. | |
| 2017/0165369 A1 | 6/2017 | Bender | |
| 2018/0169058 A1 | 6/2018 | Baltezor et al. | |
| 2018/0177739 A1 | 6/2018 | Johnson et al. | |
| 2018/0306748 A1 | 10/2018 | Seuthe | |
| 2019/0343824 A1 | 11/2019 | Baltezor et al. | |

FOREIGN PATENT DOCUMENTS

| | | |
|---|---|---|
| CN | 101129338 | 2/2008 |
| CN | 101336899 | 1/2009 |
| CN | 101829061 | 9/2010 |
| CN | 102488682 | 6/2012 |
| CN | 107281502 | 10/2017 |
| EP | 3181123 | 6/2017 |
| PT | 104693 | 1/2011 |
| TW | 201408304 | 3/2014 |
| WO | 2000/57852 | 10/2000 |
| WO | 2000/72827 | 12/2000 |
| WO | 2001/36007 | 5/2001 |
| WO | 2002/087563 | 11/2002 |
| WO | 2003/030941 | 4/2003 |
| WO | 2003/032906 | 4/2003 |
| WO | 2003/090722 | 11/2003 |
| WO | 2004/009076 | 1/2004 |
| WO | 2004/089291 | 10/2004 |

(56) References Cited

FOREIGN PATENT DOCUMENTS

| | | |
|---|---|---|
| WO | 2006/068890 | 6/2006 |
| WO | 2006/099385 | 9/2006 |
| WO | 2006/103112 | 10/2006 |
| WO | 2007/027941 | 3/2007 |
| WO | 2007/104549 | 9/2007 |
| WO | 2008/137148 | 11/2008 |
| WO | 2009/111271 | 9/2009 |
| WO | 2011/153009 | 12/2011 |
| WO | 2012/051426 | 4/2012 |
| WO | 2015/103005 | 7/2015 |
| WO | 2015/187194 | 12/2015 |
| WO | 2016/197091 | 12/2016 |
| WO | 2017/049083 | 3/2017 |
| WO | 2017/053920 | 3/2017 |
| WO | 2017/127729 | 7/2017 |
| WO | 2017/176628 | 10/2017 |
| WO | 2018/045239 | 3/2018 |
| WO | 2018/170196 | 9/2018 |
| WO | 2018/170207 | 9/2018 |
| WO | 2018/170210 | 9/2018 |
| WO | 2018/227037 | 12/2018 |
| WO | 2018/231908 | 12/2018 |

OTHER PUBLICATIONS

Socinski, M. A. "Update on taxanes in the first-line treatment of advanced non-small-cell lung cancer." Current Oncology 21.5 (2014): e691-703. (Year: 2014).*
U.S. Appl. No. 16/776,919, filed Jan. 30, 2020, Crititech, Inc.
U.S. Appl. No. 17/023,098, filed Sep. 16, 2020, Crititech, Inc.
U.S. Appl. No. 16/383,023, filed Jan. 4, 2019, Crititech, Inc.
U.S. Appl. No. 16/239,531, filed Jan. 4, 2019, Crititech, Inc.
U.S. Appl. No. 16/239,530, filed Jan. 4, 2019, Crititech, Inc.
U.S. Appl. No. 16/239,533, filed Jan. 4, 2019, Crititech, Inc.
U.S. Appl. No. 16/239,527, filed Jan. 4, 2019, Crititech, Inc.
U.S. Appl. No. 16/239,529, filed Jan. 4, 2019, Crititech, Inc.
U.S. Appl. No. 16/382,446, filed Apr. 12, 2019, Crititech, Inc.
U.S. Appl. No. 15/499,397, filed Apr. 27, 2017, Crititech, Inc.
U.S. Appl. No. 15/261,108, filed Sep. 9, 2016, Crititech, Inc.
U.S. Appl. No. 15/174,505, filed Jun. 6, 2016, Crititech, Inc.
U.S. Appl. No. 16/136,502, filed Sep. 20, 2018, Crititech, Inc.
U.S. Appl. No. 16/512,044, filed Jul. 15, 2019, Crititech, Inc.
U.S. Appl. No. 16/007,095, filed Jun. 13, 2018, Crititech, Inc.
U.S. Appl. No. 16/444,299, filed Jun. 18, 2019, Crititech, Inc.
U.S. Appl. No. 16/839,737, filed Apr. 3, 2020, Crititech, Inc.
U.S. Appl. No. 16/669,310, filed Oct. 30, 2019, Crititech, Inc.
U.S. Appl. No. 16/895,197, filed Feb. 13, 2019, Crititech, Inc.
U.S. Appl. No. 16/714,151, filed Dec. 13, 2019, Crititech, Inc.
U.S. Appl. No. 16/714,099, filed Dec. 13, 2019, Crititech, Inc.
Kirtane, et al., "EUS for pancreatuc cycstic neoplasms: The roadmap to the future us much more than just a few shades of gray," Asian Pacific Jounral of Tropical Medicine (2016) 9(12), pp. 1218-1221.
Koay et al. "Intra-tumoral heterogeneity of gemcitabine delivery and mass transport in human pancreatic cancer," Phys Biol.; 11(6): 065002 2015.
Kodumudi et. al. A novel chemoimmunomodulating property of docetaxel: suppression of myeloid-derived suppressor cells in tumor bearers. Clin. Cancer Res. 16, 4583-4594, 2010.
Lapidus et al. "Anti-tumor effect of combination therapy with intratumoral controlled-release paclitaxel (PACLIMER® Microspheres) and radiation," Prostate. 2004;58:291-298.
Lee et al. "In vivo efficacy of paclitaxel-loaded injectable in situ-forming gel against subcutaneous tumor growth," International Journal of Pharmaceutics 392 (2010) 51-56.
Lee et al, "Macrophage-Based Cell Therapies: The Long and Winding Road," J Control Release. Oct. 28, 2016; 240: 527-540.
Linghu et al. "Feasibility of Endoscopic Ultrasound-Guided OncoGel (ReGel/Paclitaxel) Injection into the Pancreas in Pigs," Endoscopy 2005; 37 (11): 1140-1142.

Liu et. al. Pre-treatment with chemotherapy can enhance the antigenicity and immunogenicity of tumours by promoting adaptive immune responses. Br. J. Cancer 102, 115-123, 2010.
Lu et. al. "Paclitaxel-loaded gelatin nanoparticle for intravesical bladder cancer therapy" Clinical Cancer Research vol. 10, Issue 22, Nov. 2004.
Lu et. al. "Paclitaxel Gelatin nanoparticles for Intravesical Bladder Cancer Therapy" The Journal of Urology vol. 185, 1478-1483, Apr. 2011.
Lu et al. "Combined PD-1 blockade and GITR triggering induce a potent antitumor immunity in murine cancer models and synergizes with chemotherapeutic drugs." Journal of translational medicine 12.1 (2014): 36.
Michaels et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice" Cancer Research 61:3689-97 (May 2001).
Manthey et al., "Taxol increases steady-state levels of lipopolysaccharide-inducible genes and protein-tyrosine phospohorylation in murine macrophages" The Journal of Immunology 149(7):2459-2465 (Oct. 1992).
Marabelle, et al. "Starting the Fight in the Tumor: expert Recommendation for the Development of Human Intratumoral Immunotherapy (HIT-IT)" Published by Oxford University Press on behalf of the European Society for Medical Oncology. 2018.
Matthes et al. "EUS-guided injection of paclitaxel (OncoGel) provides therapeutic drug concentrations in the porcine pancreas," Gastrointest Endosc. 2007;65(3):448-453.
Maude et al. "Chimeric Antigen Receptor T Cells for Sustained Remissions in Leukemia," N Engl J Med 371;16 Oct. 16, 2014.
Mayo Clinic—Patient care and health information regarding cycstic fibrosis, accessed online Sep. 10, 2018, pp. 1-8.
McGrath "Management of incidental pancreatic cysts: which guidelines?" Endoscopy International Open 2017; 05: E209-E211.
McKiernan et al, "Phase I trail of intravesical docetaxel in the management of superficial bladder cancer refractory to standard intravesical therapy" Journal of Clinical Oncology, vol. 24, No. 19, 2006.
McKiernan et. al. "Phase II Trial of intravesical nanoparticle albumin bound paclitaxel for the treatment of nonmuscle invasive urothelial carcinoma of the bladder after bacillus Calmette-guerin treatment failure" The Jounral of Urology, vol. 192, 1633-1638, 2014.
Michaels et al. "Paclitaxel promotes differentiation of myeloid-derived suppressor cells into dendritic cells in vitro in a TLR4-independent manner". J Immunotoxicol. 2012; 9:292-300.
Miele et al. "Albumin-bound formulation of paclitaxel (Abraxane® ABI-007) in the treatment of breast cancer," International Journal of Nanomedicine 2009:4 99-105.
Mills et al. "Possible Drug-Associated Pancreatitis after Paclitaxel-Cremophor Administration," Pharmacotherapy: The Journal of Human Pharmacology and Drug Therapy, vol. 20, Issue 1, Jan. 2000, pp. 95-97.
Mirvish et al. "Dendritic Cell Vaccines in Cancer: Obstacles to Overcome," Chapter 21, Dendritic Cells in Cancer, Shurin et al. (eds.) Springer Science + Business Media, LLC 2009.
Monette et al., "Chitosan thermogels for local expansion and delivery of tumor-specific T lymphocytes towards enhanced cancer immunotherapies" Biomaterials 75:237-49 (Jan. 2016).
Morales et al. "Growth-inhibiting effects on intralesional docetaxel and paclitaxel on an experimental model of malignant neuroectodermal tumor," Journal of Neuro-Oncology 59: 207-212, 2002.
Moyer et al. "Is alcohol required for the effective pancreatic cyst ablation? The prospective randomized CHARM trial Pilot study," Endoscopy International Open, 2016; 04: E603-E607.
Nars et. al. "Immunomodulatory effects of low dose chemotherapy and perspectives of its combination with immunotherapy." International journal of cancer 132.11 (2013): 2471-2478.
Necchi et al., "918TiP: Pembrolizumab and nanoparticle albumin bound paclitaxel (nabpaclitaxel) for metastatic urothelial carcinoma (UC) after chemotherapy failure: the open-label. single-arm. phase 2 PEANUT study." Annals of Oncology 42nd ESMO Congress, ESMO 2017 Madrid Spain, 28(Supplement5):v325-v326 (Sep. 2017).

(56) References Cited

OTHER PUBLICATIONS

Nsereko et al. "Localized delivery of paclitaxel in solid tumors from biodegradable chitin microparticle formulations," Biomaterials 23 (2002) 2723-2731.
Nayyar et al. "Overcoming Resistance to Natural Keller Cell Based Immunotherapies for Solid Tumors," Frontiers in Oncology, vol. 9, Article 51, Feb. 11, 2019.
O'Shaughnessy, et al. "Systemic Antitumor Immunity by PD-1/PD-L1 Inhibition Is Potentiated by Vascular—Targeted hotodynamic Therapy of Primary Tumors," Clinical Cancer Research, 24(3): 592-599, Sep. 2017.
Oh et al. "New treatment for cystic tumors of the pancreas: EUS-guided ethanol lavage with paclitaxel injection," Gastrointest Endosc. 2008;67(4):636-642.
Oh et al. "Endoscopic Ultrasonography-Guided Ethanol Lavage with Paclitaxel Injection Treats Patients with Pancreatic Cysts," Gastroenterology 2011;140:172-179.
Pettitt et al. "CAR-T Cells: A Systematic Review and Mixed Methods Analysis of the Clinical Trial Landscape," Molecular Therapy, vol. 26, No. 2, Feb. 2018.
Pitman et al. "Pancreatic Cysts Preoperative Diagnosis and Clinical Management," Cancer Cytopathology, Feb. 25, 2010, pp. 1-13, published online Dec. 30, 2009.
Pretto et al. "Preclinical evaluation of IL2-based immunocytokines supports their use in combination with dacarbazine, paclitaxel and TNF-based immunotherapy." Cancer Immunology, Immunotherapy 63.9 (2014): 901-910.
PROVENGE® Presribing Information, Rev. Jul. 2017, 2 pages.
Raju et. al. "Review of checkpoint immunotherapy for the management of non-small cell lung cancer" Immuno Targets and Therapy, 2018;7 63-75.
Rampersaud et. al. "Commentary on Hyperthermia as a treatment for bladder cancer" Oncology 2010 24(12); 1155-1160.
Ruel-Gariepy et al. "A thermosensitive chitosan-based hydrogel for the local delivery of paclitaxel," European Journal of Pharmaceutics and Biopharmaceutics 57 (2004) 53-63.
Saltus "Enhancing Immunotherapy: The Race to Make Cold Tumors Hot" published online on Apr. 27, 2018 at https://www.dana-farber.org/newsroom/publications/paths-of-progress-2018/enhancing-immunotherapy/.
Sanfilippo et al. "Phase I/II study of biweekly paclitaxel and radiation in androgen-ablated locally advanced prostate cancer," J Clin Oncol. 2008;26(18):2973-2978.
Sarr et al. "Cystic Neoplasms of the Pancreas: Benign to Malignant Epithelial Neoplasms," Surgical Clinics of North America, vol. 81, Issue 3, 1 Jun. 2001, pp. 497-509.
Sautes-Fridman et. al. "Tertiary Lymphoid Structures in Cancers: Prognostic Value, Regulation, and Manipulation for Therapeutic Intervention" Front. Immunol. 7;407, 2016.
Schumacher et. al. "Neoantigens in cancer immunotherapy" Science vol. 348, Issue 6230, Apr. 3, 2015.
Sevko Antitumor effect of paclitaxel is mediated by inhibition of myeloid-derived suppressor cells and chronic inflammation in the spontaneous melanoma model. J. Immunol. 190,2464-2471 (2013).
Sevko et al. Application of paclitaxel in low non-cytotoxic doses supports vaccination with melanoma antigens in normal mice. J Immunotoxicol. Jul.-Sep. 2012;9(3):275-81.
Shepard et al. "Phase II trial of neoadjuvant nab-paclitaxel in high risk patients with prostate cancer undergoing radical prostatectomy," J Urol. 2009;181:1672-1677.
Shi el al. "PD-1 Blockade Boosts Radiofrequency Ablation-Elicited Adaptive Immune Responses against Tumor" Clin. Cancer Res; 22(5); 1179-84, 2016.
U.S. Appl. No. 16/669,692, filed Oct. 31, 2019, Crititech, Inc.
U.S. Appl. No. 16/834,155, filed Mar. 30, 2020, Crititech, Inc.
FDA—"ABRAXANE—Prescribing Information" Oct. 1, 2012, pp. 1-19.
Gradishar, "Taxanes for the Treatment of Metastatic Breast Cancer" Breast Cancer: Basic and Clinical Research 6 (1):159-71 (Jan. 2012).

Amiji et al. "Intratumoral Administration of Paclitaxel in an in Situ Gelling Poloxamer 407 Formulation," Pharmaceutical Development and Technology, 7(2), 129-202 (2002).
Anastasiadis et. al. "Best practice in the treatment of nonmuscle invasive bladder cancer" Ther Adv Urol (2012) 4(1) 13-32.
Arnone et al. "Commentary: Current status of intratumoral therapy for glioblastoma," J Neurol Neuromed (2016) 1(6): 27-31.
Asmawi et al. "Excipient selection and aerodynamic characterization of nebulized lipid-based nanoemulsion loaded with docetaxel for lung cancer treatment", Drug Delivery and Translational Research, vol. 9, No. 2, Apr. 2018, pp. 543-554.
Atar et al. "EUS Guided Injection of Albumin Bound Paclitaxel Into Mucinous Pancreatic Cysts," Gastrointestinal Endoscopy, vol. 81, No. 5S : 2015.
Axiak-Bechtel et al. "Nanoparticulate paclitaxel demonstrates antitumor activity in PC3 and Ace-1 aggressive prostate cancer cell lines," Invest New Drugs. 2013;31:1609-1615.
Bharadwaj et al. "Topical delivery of paclitaxel for treatment of skin cancer," Drug Development and Industrial Pharmacy,vol. 42, No. 9, Mar. 2016, pp. 1482-1494.
Bilusic et. al. "Immunotherapy of Prostate Cancer: Facts and Hopes", Clin Cancer Res; 23(22); 6764-70, 2017.
Bracci et al. "Immune-Based mechanisms of cytotoxic chemotherapy: implications for the design of novel and rationale-Based combined treatments against cancer." Cell Death and Differentiation, vol. 21, No. 1, 2013, pp. 15-25., doi:10.1038/cdd.2013.67.
Buda et. al. "Randomised controlled trial comparing single agent paclitaxel vs epidoxorubicin plus paclitaxel in patients with advanced ovarian cancer in early progression after platinum-based chemotherapy", British Journal of Cancer (2004) 90, 2112-2117.
Butterfield "Cancer vaccines" BMJ. 2015; 350; h988.
Cao et. al. "Tumor associated macrophages and angiogenesis dual-recognizable nanoparticles for enhanced cancer chemotherapy" Nanomedicine: Nanotechnology, Biology, and Medicine 14 (2018) 651-659.
Celegene "What is the optimal chemotherapy partner for immune checkpoint inhibitor drugs?" Presentation Mar. 16, 2017 by Eric Raymond at Mediterranean Institute for Life Sciences, Republic of Croatia, 73 pages.
Chan et. al. "The immunological effects of taxanes". Cancer Immunol. Immunother. Jul. 2000;49(4-5):181-5.
Chen et. al. "Chemoimmunotherapy: reengineering tumor immunity". Cancer Immunol. Immunother. 62, 203-216, 2013.
Choi et al. "Long-term outcomes after endoscopic ultrasound-guided ablation of pancreatic cysts," Endoscopy, 2017; 49: 866-873.
clintrials.gov "A study of Pembrolizumab (MK-3475) in combination with chemotherapy or immunotherapy in participants with lung cancer" Jan. 16, 2014.
Colbeck et. al. "Tertiary Lymphoid Structures in Cancer: Drivers of Antitumor Immunity, Immunosuppression, or Bystander Sentinels in Disease?" Front Immunol, 8, 1830. doi:10.3389/fimmu.2017.01830.
Desai et al. "Improved effectiveness of nanoparticle albumin-bound (nab) paclitaxel versus polysorbate-based docetaxel in multiple xenografts as a function of HER2 and SPARC status," Anti-Cancer Drugs 2008, 19:899-909.
Desai et al. "Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel," Clin Cancer Res 2006;12(4).
Dewitt et al. "Alteration in cyst fluid genetics following endoscopic ultrasound-guided pancreatic cyst ablation with ethanol and paclitaxel," Endoscopy 2014; 46(06): 457-464.
Dewitt "Pancreatic cyst ablation: why are we not doing more of these procedures?" Endoscopy, 2017; 49: 839-841.
Diaz et al. "Concomitant combination of active immunotherapy and carboplatin-or paclitaxel-based chemotherapy Improves anti-tumor response." Cancer Immunology, Immunotherapy 62.3 (2013): 455-469.
Eisenhauer et. al. "New response evaluation criteria in solid tumours: Revised RECIST guideline (version 1.1)" European Jounral of Cancer 45 (2009) 228-247.

(56) References Cited

OTHER PUBLICATIONS

Elstad et al. "OncoGel (ReGelipaclitaxel)—Clinical applications for a novel paclitaxel delivery system," Advanced Drug Delivery Reviews 61 (2009) 785-794.
Engels et al. "Alternative drug formulations of docetaxel: a review," Anti-Cancer Drugs 2007 18:95-103.
Farrell "Prevalence, Diagnosis and Management of Pancreatic Cystic Neoplasms: Current Status and Future Direction," Gut and Liver, vol. 9, No. 5, Sep. 2015, pp. 571-589.
Farrell et al. "Pancreatic Cystic Neoplasms: Management and Unanswered Questions," Gastroenterology 2013;144:1303-1315.
Ferenbach et. al. "Macrophages and dendritic cells: what is the difference?" Kidney International (2008) 74.
Finkelstein et. al. "Serial assessment of lymphocytes and apoptosis in the prostate during coordinated intraprostatic dendritic cell injection and radiotherapy" Immunotherapy (2012) 4 (4), 373-382.
Forde et. al. "Neoadjuvant PD-1 Blockade in Resectable Lung Cancer" N Engl J Med 2018; 378;1976-86.
Gajewski "Fast Forward—Neoadjuvant Cancer Immunotherapy" N Engl J Med 378;21 May 24, 2018, 2034-35.
Galluzzi et. al. The secret ally: immunostimulation by anticancer drugs. Nat. Rev. Drug Discov. 11, 215-233, 2012.
Garnett et. al. "Combination of docetaxel and recombinant vaccine enhances T-cell responses and antitumor activity: effects of docetaxel on immune enhancement." Clinical Cancer Research 14.11 (2008): 3536-3544.
Goldberg et al. "Intratumoral cancer chemotherapy and immunotherapy: opportunities for nonsystemic preoperative drug delivery," JPP 2002, 54: 159-180.
Gomez et al. "EUS-guided ethanol lavage does not reliably ablate pancreatic cystic neoplasms," Gastrointestinal Endoscopy vol. 83, No. 5 : 2016.
Govindan et al. "Phase III trial of ipilimumab combined with paclitaxel and carboplatin in advanced squamous non-small-cell lung cancer" Journal of Clinical Oncology (2017): JCO-2016.
Gruden et al., "Antitumoral effect and reduced systemic toxicity in mice after intra-tumoral injection of an in vivo solidifying calcium sulfate formulation with docetaxel", European Journal of Pharmaceutics and Biopharmaceutics, 114 (2017); 186-193.
Grünwald et al. "The role of nephrectomy in metastatic renal cell carcinoma" Nature Reviews Nephrology 14(10):601-602 (Oct. 2018).
Gu et al. "Nanoformulation of paclitaxel to enhance cancer therapy," Journal of Biomaterials Applications 28(2) 198-307 2012.
Gulley et. al. "Phase I study of intraprostatic vaccine administration in men with locally recurrent or progressive prostate cancer". Cancer Immunol Immunother, 2013;62,1521-1531.
Hosein et al. "A phase II trial of nab-Paclitaxel as second-line therapy in patients with advanced pancreatic cancer. Am J Clin Oncol," Apr. 1, 2013; 36(2):151-6.
Hussain et al. "Long-term follow-up of a prospective trial of trimodality therapy of weekly paclitaxel, radiation, and androgen deprivation in high-risk prostate cancer with or without prior prostatectomy," Int J Radiation Oncology Biol Phys. 2012;82(1)167-174.
Indolfi et al. "A tunable delivery platform to provide local chemotherapy for pancreatic ductal adenocarcinoma. Biomaterials," 2016;93:71-82.
"Inman, ""Atezolizumab/Nab-Paclitaxel Combo Shows High Response Rates in TNBC"". Internet Citation. Dec. 10, 2015. Retrieved from the Internet:URL:http://www.onclive.comjconference-coverage/sabcs-2015/ atezolizumab-nab-paclitaxel-combo-shows-high-response-rates-in-tnbc [retrieved Oct. 20, 2017].".
Jackson et al. "The Suppression of Human Prostate Tumor Growth in Mice by the Intratumoral Injection of a Slow-Release Polymeric Paste Formulation of Paclitaxel," Cancer Research 60, 4146-4151, Aug. 1, 2000.
Janeway et al. "Using the immune response to attack tumors," Immunobiology: The Immune System in Health and Disease, 5th ed, New York: Garland Science; 2001.
Javeed et. al. Paclitaxel and immune system. Eur J Pharm Sci. Nov. 5, 2009;38(4):283-90.
Kakran Mitali, et al., "Modified supercritical antisolvent method with enhanced mass transfer to fabricate drug nanoparticles," Materials Science and Engineering, 33(5): 2864-2870, Mar. 2013.
Lee, et al., "Supercritical antisolvent production of biodegradable micro-and nanoparticles for controlled delivery of paclitaxel," Journal of Controlled Release, 125(2): 96-106, Oct. 2007.
International Search Report and Written Opinion for PCT/US2016/035993, dated Sep. 19, 2016.
Merisko-Liversidge, et al., "Formulation and Antitumor Activity Evaluation of Nanocrystalline Suspensions of Poorly Soluble Anticancer Drugs," Pharmaceutical Research, 13(2): 272-278, 1996.
Merisko-Liversidge, et al., "Nanosizing: a formulation approach for poorly-water-soluble compounds," European Journal of Pharmaceuticals Sciences, 18 (2003): 113-120.
Crown et al., "Docetaxel and Paclitaxel in the Treatment of Breast Cancer: A review of clinical experience" The Oncologist (2004) vol. 9(2), pp. 24-32.
Williamson, et al., "Phase I clinical trial of the intraperitoneal {IP} administration of a novel nanoparticle formulation of paclitaxel (NTX)," Poster Presentation, ACS, Sep. 2013.
Johnston, et al., "Nanotax Injectable Nanocystal Paclitaxel for Ovarian and Other Intraperitoneal Cancers," Datasheet, Sep. 2013.
Bouquet, et al., "Drug Delivery of paclitaxel for an intraperitoneal chemotherapy," Thesis, 2009.
Della Porta and Reverchon, "Engineering Powder Properties by supercritical fluid for optimum Drug Delivery, Part One: Supercritical Antisolvent Precipitation," BioProcessTechnical, Feb. 2005, 48-52.
Della Porta and Reverchon, Engineering Powder Properties by supercritical fluid for optimum Drug Delivery, Part Two: Supercritical-Assisted Atomization, BioProcess Technical, Mar. 2005, 54-60.
Charoenchaitrakool, et al., "Micronization by Rapid Expansion of Supercritical Solutions to Enhance the Dissolution Rates of Poorly Water-Soluble Pharmaceuticals," Ind Eng Chem Res, 2000, 39: 4794-4802.
Werth, et al., "Agglomeration of Charged Nanopowders in Suspensions," Phys Rev E Stat Nonlin Soft Matter Phys. Feb. 2006;73(2 Pt 1):021402. Epub Feb. 10, 2006.
Rasenack, et al., Micronization of Anti-Inflammatory Drugs for Pulmonary Delivery by a Controlled Crystallization Process, J Pharm Sci, 92:35-44, 2003.
Castellanos, "The relationship between attractive interparticles forces and bulk behaviors in dry and uncharged fine powders," Advances in Physics, 54(4): 263-376, 2005.
Snavely, et al., "Micronization of insulin from halogenated alcohol solution using supercritical carbon dioxide as an antisolvent," J Pharm Sci, 91:2026-2039, 2002.
Vemavarapu, Particle formation by rapid expansion of supercritical solutions, Dissertation 2002.
Podczeck, "The Influence of Particle Size Distribution and Surface Roughness of Carrier Particles on the in vitro Properties of Dry Powder Inhalations," Aerosol Science and Technology, 31(4): 301-321, 1999.
Young, Characterisation of particle-particles interactions using the atomic force microscope, Dissertation, 2002.
Barura, et al "Challenges associated with penetration of nanoparticles across cell and tissue barriers: A review of current status and future prospects," Nano Today, 9: 223-243, 2014.
Carbone, et al "Non-Small Cell Lung Cancer: Role of the Immune System and Potential for Immunotherapy," J Thorac Oncol, 10(7): 974-984, 2015.
Desai, et al, "Pulmonary delivery of a novel, cremophor-free, protein-based nanoparticle preparation of paclitaxel," Proceedings of the American Association for Cancer Research, 44: 731-732, Abstract 2003.
Hershey, et al, "Inhalation Chemotherapy for Macroscopic Primary or Metastatic Lung Tumors: Proof of Principle Using Dogs with Spontaneously Occurring Tumors as a Model," Clinical Cancer Research, 5:2653-2659, 1999.

(56) References Cited

OTHER PUBLICATIONS

Hiraoka, et al, "Concurrent infiltration by CD8+T cells and CD4+T cells is a favourable prognostic factor in non-small-cell lung carcinoma," British Journal of Cancer, 94: 275-280, 2006.
Hohenforst-Schmidt, "Intratumoral chemotherapy for lung cancer: re-challenge current targeted therapies," Drug Design, Development and Therapy, 571-583, 2013.
Koshkina, et al "Paclitaxel Liposome Aerosol Treatment Induces Inhibition of Pulmonary Metastases in Murine Renal Carcinoma Model," Clinical Cancer Research, 7: 3258-3262, Mar. 2001.
Koshkina, et al, "Improved respiratory delivery of the anticancer drugs, camptothecin and paclitaxel, with 5% CO2-enriched air: pharmacokinetic studies," Cancer Chemother Pharmacol, 47: 451-456, Oct. 2001.
Koshkina, et al, "Cyclosporin A Aerosol Improves the Anticancer Effect of Paclitaxel Aerosol in Mice," Journal of Aerosol Medicine, 17(1): 7-14, 2004.
Kulkarni, et al, "The Use of Systemic Treatment in the Maintenance of Patients with Non-Small Cell Lung Cancer: A Systematic Review," Journal of Thoracic Oncology, 11(7): 989-1002, 2016.
Liu, et al, "Paclitaxel Nanocrystals for Overcoming Multidrug Resistance in Cancer," Mol Pharm, 7(3): 863-869, 2010.
Liu, et al, "Enabling Anticancer Therapeutics by Nanoparticle Carriers: The Delivery of Paclitaxel," Int J. Mol. Sci., 12:4395-4413, 2011.
Mallow, et al, Broncho-Adventitial Delivery of Paclitaxel to Extend Airway Patency in Malignant airway Obstruction (broadway trial), Advances in Thoracic Oncologic Diagnostics, Abstract May 2017.
Polo, et al, "Maintenance strategies in stage IV non-small-cell lung cancer (NSCLC): in which patients, with which drugs?" Annals of Oncology 25: 1283-1293, Dec. 2013.
Wakabayashi, et al, "CD4+ T cells in cancer stroma, not CD8+ T cells in cancer cell nests, are associated with favorable prognosis in human non-small cell lung cancers," Cancer Sci, 94(11): 1003-1009, Nov. 2003.
Xing, et al, "Efficacy and safety of albumin-bound paclitaxel in treating recurrent advanced non-small-cell lung cancer," Chinese Journal of Cancer Research, 25(2):200-205, 2013.
Zarogoulidis, et al, "Inhaled chemotherapy in lung cancer: future concept of nanomedicine," International Journal of Nanomedicine, 7: 1551-1572, Mar. 2012.
Zhou, "Atomized paclitaxel liposome inhalation treatment of bleomycin-induced pulmonary fibrosis in rats," Genetics and Molecular Research, 15(2): 1-11, 2016.
Kalos et al. "T Cells with Chimeric Antigen Receptors Have Potent Antitumor Effects and Can Establish Memory in Patients with Advanced Leukemia," Sci Transl Med. Aug. 10, 2011; 3(95) 95ra73.
Khullar et al. "Nanoparticle Migration and Delivery of Paclitaxel to Regional Lymph Nodes in a Larch Animal Model," J Am Coll Surg. Mar. 2012; 214(3): 328-337.
De Smet el al., "Development of a Nanocrystalline Paclitaxel Formulation for Hipec Treatment" Pharm. Research 29:2398-2406 (2012).
NSST Technical Report, 1503-1, URL: htlps:/lwww.nsst.nssmc.com/techrepo/zairyo pdf/H RM-1503.pdf.
Shurin et al. "Cancer Therapy and Dendritic Cell Immunomodulation," Chapter 14, Dendritic Cells in Cancer, Shurin et al. (eds.) Springer Science + Business Media, LLC 2009.
Slovin "Chemotherapy and immunotherapy combination in advanced prostate cancer." Clin Adv Hematol Oncol 10.2 (2012): 90-100.
Soliman "nab-Paclitaxel as a potential partner with checkpoint inhibitors in solid tumors" Onco Targets and Therapy 10:101-112 (Dec. 2016).
Stark et al. "Pancreatic Cyst Disease A Review," JAMA May 3, 2016 vol. 315, No. 17.
Swartz et al. "Lymphatic and interstitial flow in the tumor microenvironment: linking mechanobiology with immunity," Nature Reviews Cancer, vol. 12, Mar. 2012.
Tanaka et al. "Clinical aspects of intraductal papillary mucinous neoplasm of the pancreas," J Gastroenterol 2005; 40:669-675.
Tanaka et al. "International consensus guidelines 2012 for the management of IPMN and MCN of the pancreas," Pacreatology 12 (2012) 183-197.
Tanaka "Current best practice and controversies in the follow up of patients with asymptomatic branch duct IPMN of be pancreas," HPB 2016, 18, 709-711.
Van Soest et al. "Irrefutable evidence for the use of docetaxel in newly diagnosed metastatic prostate cancer: results from the STAMPEDE and CHAARTED trials," BMC Medicine (2015) 13:304.
Vanneman et. al. Combining immunotherapy and targeted therapies in cancer treatment. Nat. Rev. Cancer 12, 237-251, 2012.
Vaz-Luis et. al. "Survival Benefit Needed to Undergo Chemotherapy: Patient and Physician Preferences" Cancer Aug. 1, 2017, 2821-2828, published online Mar. 21, 2017 in Wiley Online Library (wileyonlinelibrary.com).
Vukelja et al. "Phase 1 study of escalating-dose OncoGel (ReGel/paclitaxel) depot injection, a controlled-release formulation of paclitaxel, for local management of superficial solid tumor lesions. Anticancer Drugs," 2007;18(3): 283-9.
Wang et al. "Intratumoral Injection of Taxol In Vivo Suppresses A549 Tumor Showing Cytoplasmic Vacuolization," Journal of Cellular Biochemistry 113:1397-1406 (2012).
Weiss et al. "A phase lb study of pembrolizumab plus chemotherapy in patients with advanced cancer (PembroPlus)." British Journal of Cancer (2017).
Worley et. al. "Docetaxel accumulates in lymphatic circulation following subcutaneous delivery compared to intravenous delivery in Rats" Anticancer Research 36; 5071-5078 (2016).
Wysham et al. "Adding bevacizumab to single agent chemotherapy for the treatment of platinum-resistant recurrent ovarian cancer: A cost effectiveness analysis of the AURELIA trial" Gynecologic Oncology 145 (2017) 340-345.
Yoo et al. "An In Vivo Evaluation of Docetaxel Delivered Intratumorally in Head and Neck Squamous Cell Carcinoma," Arch Otolaryngol Head Neck Surg/vol. 131, May 2005.
Yu et al. "Tumor-immune profiling of murine syngeneic tumor models as a framework to guide mechanistic studies and predict therapy response in distinct tumor microenvironments," PLOS ONE https://doi.org/10.1371/journal.pone.0206223 Nov. 2, 2018.
Zentner et al. "Biodegradable block copolymers for delivery of proteins and water-insoluble drugs," Journal of Controlled Release 91 (2001) 203-215.
Zhang et al. MTDH/AEG-1 based DNA vaccine suppresses metastasis and enhances chemosensitivity to paclitaxel in pelvic lymph node metastasis Biomedicine & Pharmacotherapy 70 (2015) 217-226.
Zhang et al. "Endoscopic ultrasound-guided ethanol ablation therapy for tumors," World J Gastroenterol Jun. 14, 2013; 19(22): 3397-3403.
Zhao et al. "Preparation of superparamagnetic paclitaxel nanoparticles from modified chitosan and their cytotoxicity against malignant brain glioma," English Abstract, Journal of Biomedical Engineering Jun. 1, 2011, 28(3):513-516 (lang: chi).
Zhao et. al. "New Avenues for Nanoparticle-Related Therapies" Nanoscale Research Letters (2018) 13;136.
Zheng et. al. "Chemotherapy-induced immunomodulation in non-small-cell lung cancer: a rationale for combination chemoimmunotherapy" Immunotherapy (2017) 9(11), 913-927.
Zhong et al., "Low-dose paclitaxel prior to intrtumoral dendtritic cell vaccine modulates intratumoral cytokine network and lung cancer growth" Clinical Cancer Research 13(18):5455-62 (Sep. 2007).
Zhou et al. "Highly penetrative, drub-loaded nanocarriers improve treatment of glioblastoma," PNAS, Jul. 16, 2013, vol. 110, No. 29, 11751-11756.
Zitvogel et. al. "Mechanism of action of conventional and targeted anticancer therapies: reinstating immunosurveillance." Immunity 39.1 (2013): 74-88.
Al-Ghananeem et al. "Intratumoral Delivery of Paclitaxel in Solid Tumor from Biodegradable Hyaluronan Nanoparticle Formulations," AAPS PharmSciTech, vol. 10, No. 2, Jun. 2009.
clinicaltrials.gov "OGX-011 and Docetaxel in Treating Patients with Metastatic or Locally Recurrent Solid Tumors" May 10, 2007.

(56) References Cited

OTHER PUBLICATIONS

Goel, et al., "Exploring targeted pulmonary delivery for treatment of lung cancer," IntJ Phami Investig (2013) 3 (1):8-14.

Lu Shengjie et al: "Mucoadhesive polyacrylamide nanogel as a potential hydrophobic drug carrier for intravesical bladder cancer therapy", European Journal of Pharmaceutical Sciences, vol. 72, Mar. 2015, pp. 57-68.

Pazdur, et al., (The toxoids: paclitaxel (Taxol) and docetaxel (Taxotere, Cancer treatment reviews, 19(4): 351-386 (1993).

Shikanov A et al: "Paclitaxel tumor biodistribution and efficacy after intratumoral injection of a biodegradable extended release implant", International Journal of Pharmaceutics, vol. 358, No. 1-2, Jun. 2008, pp. 114-120.

Shikanov et al. "Intratumoral Delivery of Paclitaxel for Treatment of Orthotopic Prostate Cancer," Journal of Pharmaceutical Sciences, vol. 98, No. 3, Mar. 2009.

Ze Lu et al, "Paclitaxel Gelatin Nanoparticles for Intravesical Bladder Cancer Therapy," Journal of Urology, vol. 185, No. 4, Apr. 2011, pp. 1478-1483.

Nadezhda V Koshkina et al: "Paclitaxel Liposome Aerosol Treatment Induces Inhibition of Pulmonary Metastases in Murine Renal Carcinoma Model", Clinical Cancer Research, Oct. 2001, pp. 3258-3262.

Le Visage, et al.,"Efficacy of PaclitaxelReleased From Bio-Adhesive Polymer Microspheres on Model Superficial Bladder Cancer," Journal of Urol, vol. 171, No. 3, Mar. 2004, pp. 1324-1329.

Sharma, et al., "Development of Stabilized Paclitaxel nanocrystals: In vitro and in vivo efficacy studies," European Jounral of Pharmaceuticals Science, 69: 51-60, Jan. 2015.

Pankaj, et al. Nanosized Paclitaxel Particles from Supercritical Carbon Dioxide Processing and Their Biological Evaluation, LANGMUIR, 23(5): 2674-2679, Feb. 2007.

Deng et al. "Understanding the Structure and Stability of Paclitaxel nanocrystals," Int J Pharm May 10, 2010, 390 (2): 242-249.

Feng et al. "A critical review of lipid-based nanoparticles for taxane delivery," Cancer Letters 334 (2013) 157-175.

Ghosh et al. "Nanosuspensions for improving the bioavailability of a poorly soluble drug and screening of stabilizing agents to inhibit crystal growth," International Journal of Pharmaceutics 409 (2011) 260-268.

Ma et al. "Paclitaxel Nano-Delivery Systems: A Comprehensive Review," Journal of Nanomedicine and Nanotechnology, vol. 4, No. 2, 2013 pp. 1-35.

Muller et al. "Challenges and solutions for the delivery of biotech drugs—a review of drug nanocrystal technology and lipid nanoparticles," Journal of Biotechnology 113 (2004) 151-170.

Narang et al. "Pharmaceutical development and regulatory considerations for nanoparticles and nanoparticulate drug delivery systems," Journal of Pharmaceutical Sciences 2013.

Pathak et al. "Nanosized Paclitaxel Particles from Supercritical Carbon Dioxide Processing and Their Biological Evaluation," Langmuir, 23(5): 2674-2679, Feb. 2007.

Ranade et al. "Clinical and economic implications of the use of nanoparticle paclitaxel (Nanoxel) in India," Ann. Oncol. 24:v6-v12 (2013).

Surapaneni et al. "Designing Paclitaxel Drug Delivery Systems Aimed at Improved Patient Outcomes: Current Status and Challenges," ISRN Pharmacology, vol. 2012.

Wu et al. "Physical and chemical stability of drug nanoparticles," Advanced Drug Delivery Reviews 63 (2011) 456-469.

\* cited by examiner

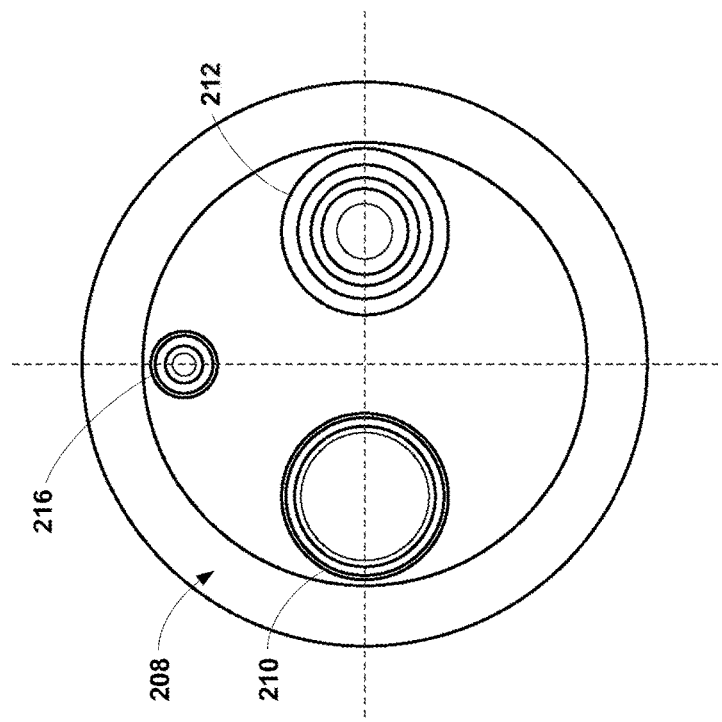
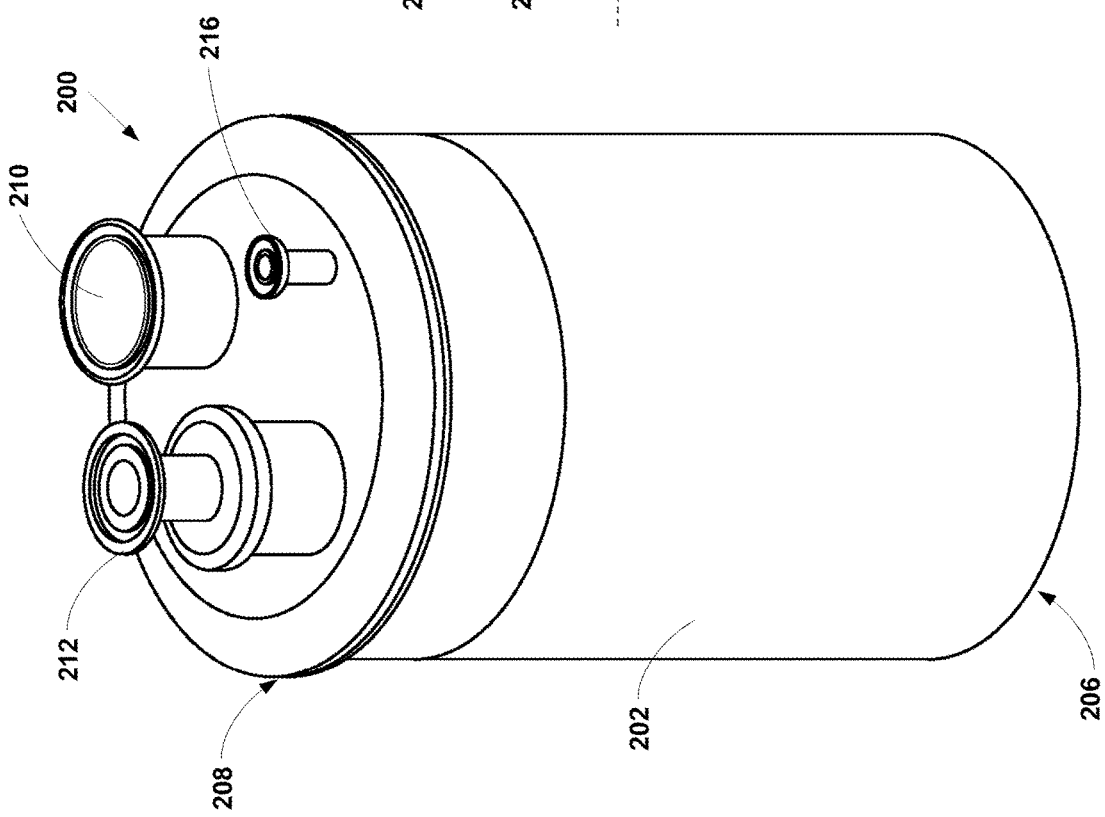

TAXANE PARTICLES AND THEIR USE

CROSS REFERENCE

This application is a continuation of U.S. application Ser. No. 16/669,310 filed Oct. 30, 2019, which is a continuation of U.S. application Ser. No. 15/895,197 filed Feb. 13, 2018, now U.S. Pat. No. 10,507,195 issued Dec. 17, 2019, which is a continuation of U.S. application Ser. No. 15/499,397 filed Apr. 27, 2017, now U.S. Pat. No. 9,918,957 issued which Mar. 20, 2018, which is a continuation of U.S. application Ser. No. 15/261,108 filed Sep. 9, 2016, which is a divisional of U.S. patent application Ser. No. 15/174,505 filed Jun. 6, 2016, now U.S. Pat. No. 9,814,685 issued Nov. 14, 2017, which claims priority to U.S. Provisional Patent Application Ser. Nos. 62/171,060 filed Jun. 4, 2015, 62/171,001 filed Jun. 4, 2015, and 62/171,008 filed Jun. 4, 2015, each incorporated by reference herein in its entirety.

BACKGROUND

Dissolution rate is a key parameter in determining the rate and extent of drug absorption and bioavailability. Poor aqueous solubility and poor in vivo dissolution are limiting factors for in vivo bioavailability of many drugs. Thus, in vitro dissolution rates are recognized as an important element in drug development, and methods and compositions for increasing the dissolution rates of poorly soluble drugs are needed.

SUMMARY OF THE INVENTION

In a first aspect, the invention provides compositions, comprising particles including at least 95% by weight of a taxane, or a pharmaceutically acceptable salt thereof, wherein the particles have one or both of the following characteristics:

(i) a mean bulk density between about 0.050 g/cm$^3$ and about 0.15 g/cm$^3$, and/or;

(ii) have a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g.

In one embodiment, the taxane is selected from the group consisting of paclitaxel, docetaxel, cabazitaxel, taxadiene, baccatin III, taxchinin A, brevifoliol, and taxuspine D, or a pharmaceutically acceptable salt thereof. In another embodiment, the taxane is selected from the group consisting of paclitaxel, docetaxel, and cabazitaxel, or a pharmaceutically acceptable salt thereof.

In a further embodiment, the taxane is paclitaxel or a pharmaceutically acceptable salt thereof, and wherein the particles have a mean bulk density between about 0.050 g/cm$^3$ and about 0.12 g/cm$^3$, or between about 0.060 g/cm$^3$ and about 0.11 g/cm$^3$. The paclitaxel particles may have a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g. The paclitaxel particles may have a SSA of between about 22 m$^2$/g and about 40 m$^2$/g, 25 m$^2$/g and about 40 m$^2$/g, 30 m$^2$/g and about 40 m$^2$/g, or between about 35 m$^2$/g and about 40 m$^2$/g. The paclitaxel particles may have a bulk density of between about 0.060 g/cm$^3$ and about 0.11 g/cm$^3$ and a SSA of between about 22 m$^2$/g and about 40 m$^2$/g. In another embodiment, at least 40% (w/w) of the paclitaxel is dissolved in 30 minutes or less in a solution of 50% methanol/50% water ((v/v)) at 37° C. and pH 7.0 in a USP II paddle apparatus operating at 75 RPM.

In one embodiment, the taxane is docetaxel or a pharmaceutically acceptable salt thereof, and wherein the particles have a mean bulk density between about 0.050 g/cm$^3$ and about 0.12 g/cm$^3$, or between about 0.06 g/cm$^3$ and about 0.1 g/cm$^3$. The docetaxel particles may have a SSA of at least 18 m$^2$/g, 20 m$^2$/g, 25 m$^2$/g, 30 m$^2$/g, 35 m$^2$/g, 40 m$^2$/g, or 42 m$^2$/g. The docetaxel particles may have a SSA of between about 40 m$^2$/g and about 50 m$^2$/g, or between about 43 m$^2$/g and about 46 m$^2$/g. The docetaxel particles may have a bulk density of between about 0.06 g/cm$^3$ and about 0.1 g/cm$^3$ and a SSA of between about 40 m$^2$/g and about 50 m$^2$/g. In a further embodiment, at least 20% (w/w) of the docetaxel is dissolved in 30 minutes or less in a solution of 15% methanol/85% water (v/v) at 37° C. and pH 7.0 in a USP II paddle apparatus operating at 75 RPM.

In a further aspect, the invention provides compositions comprising particles including at least 95% by weight of paclitaxel, or a pharmaceutically acceptable salt thereof, wherein the particles have a specific surface area (SSA) of at least 12 m$^2$/g. The paclitaxel particles may have a SSA of at least 12 m$^2$/g, 15 m$^2$/g, 20 m$^2$/g, 25 m$^2$/g, 30 m$^2$/g, 32 m$^2$/g, 34 m$^2$/g, or 35 m$^2$/g. In one embodiment, at least 40% (w/w) of the paclitaxel is dissolved in 30 minutes or less in a solution of 50% methanol/50% water (v/v) at 37° C. and pH 7.0 in a USP II paddle apparatus operating at 75 RPM.

In another aspect, the invention provides compositions comprising particles including at least 95% by weight of paclitaxel, wherein at least 40% (w/w) of the paclitaxel is dissolved in 30 minutes or less in a solution of 50% methanol/50% water (v/v) in a USP II paddle apparatus operating at 75 RPM. The invention also provides compositions comprising including at least 95% by weight of docetaxel, wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

The compositions of the invention may comprise particles have a mean particle size of between about 0.4 µm and about 1.2 µm, or between about 0.6 µm and about 1.0 µm. The particles may be uncoated and exclude polymer, protein, polyethoxylated castor oil and polyethylene glycol glycerides composed of mono-, di- and triglycerides and mono- and diesters of polyethylene glycol. The compositions may further be incorporated into a suspension, which further comprises a pharmaceutically acceptable aqueous carrier. The composition may further comprise one or more components selected from the group consisting of polysorbate, methylcellulose, polyvinylpyrrolidone, mannitol, and hydroxypropyl methylcellulose. The compositions may comprise by weight at least 96%, 97%, 98%, 99%, or 100% of the compound.

The invention further provides methods for treating a tumor, comprising administering to a subject with a tumor an amount effective to treat the tumor of a composition according to any embodiment or combination of embodiments of the invention. In one embodiment, the tumor may be selected from the group consisting of a breast tumor, an ovarian tumor, a lung tumor, a bladder tumor, a prostate tumor, a bone tumor, a stomach tumor and a pancreatic tumor. In another embodiment, the composition is administered intraperitoneally, such as by perfusion or as a bolus into the peritoneal cavity. In one embodiment, the intraperitoneal administration is initiated after removal of ascites fluid from the peritoneal cavity. In another embodiment, the subject is a human subject.

The invention further provides methods for making compound particles, comprising:

(a) introducing (i) a solution comprising at least one solvent and at least one solute comprising a compound of interest into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% during the passing, and wherein the nozzle orifice has a diameter of between 20 μm and 125 μm; and (c) contacting the atomized droplets with the compressed fluid, to cause depletion of the solvent from the atomized droplets, to produce compound particles, wherein steps (a), (b), and (c) are carried out under supercritical temperature and pressure for the compressed fluid.

In one embodiment, the method further comprises:

(d) contacting the atomized droplets produced in step (c) with an anti-solvent to cause further depletion of the solvent from the compound particles, wherein step (d) is carried out under supercritical temperature and pressure for the anti-solvent.

In one embodiment, a flow rate of the solution through the nozzle has a range from about 0.5 mL/min to about 30 mL/min. In a further embodiment, the sonic energy source comprises one of a sonic horn, a sonic probe, or a sonic plate. In another embodiment, the sonic energy source has a frequency between about 18 kHx and about 22 kHz, or about 20 kHz.

The methods may further comprise:

(e) receiving the plurality of particles through the outlet of the pressurizable chamber; and (f) collecting the plurality of particles in a collection device.

In one embodiment, the compound is a taxane. The method of any one of claims 30-35 wherein the compound is a taxane. Exemplary taxanes may include paclitaxel, docetaxel, cabazitaxel, taxadiene, baccatin III, taxchinin A, brevifoliol, and taxuspine D, or a pharmaceutically acceptable salt thereof. In a specific embodiment, the taxane is selected from the group consisting of paclitaxel, docetaxel, and cabazitaxel, or a pharmaceutically acceptable salt thereof. In one embodiment, the solvent is selected from the group consisting of acetone, ethanol, methanol, dichloromethane, ethyl acetate, chloroform, acetonitrile, and suitable combinations thereof. In various embodiments, the compressed fluid and/or the anti-solvent may be super critical carbon dioxide. In one embodiment, the compound is paclitaxel and the solvent comprises acetone. In another embodiment, the compound is docetaxel and the solvent comprises ethanol. In a further embodiment, the method is carried out between 31.1° C. to about 60° C., and at between about 1071 psi and about 1800 psi.

The invention also provides compound particles prepared by the method of any embodiment or combination of embodiments of the invention.

BRIEF DESCRIPTION OF THE FIGURES

FIG. 5 illustrates a perspective view of a particle collection device, according to an example embodiment.

FIG. 6 illustrates a top view of the particle collection device, according to an example embodiment.

DETAILED DESCRIPTION OF THE INVENTION

Figure 1:
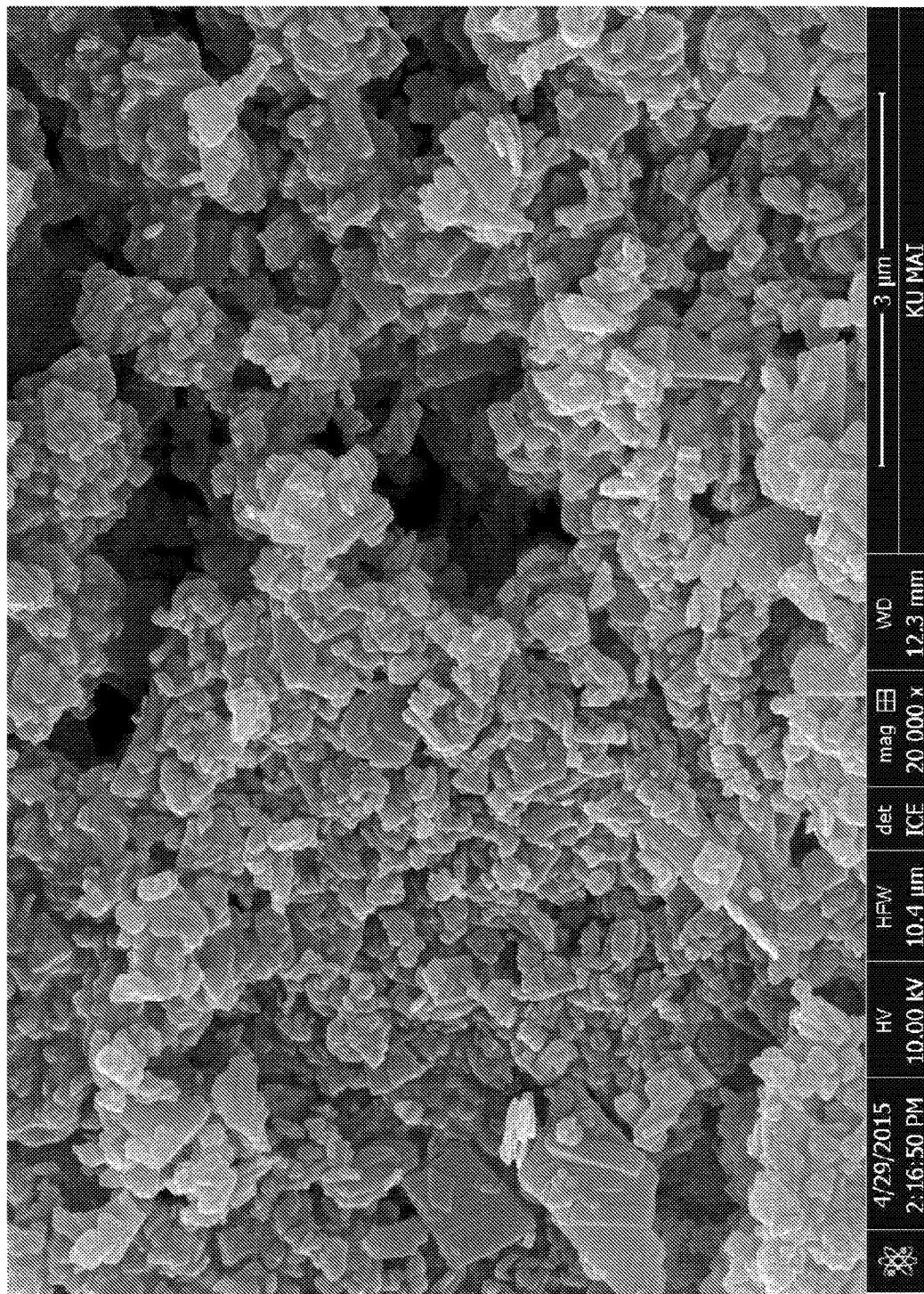
FIG. 1 is an electron micrograph of exemplary paclitaxel particles of the invention.

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise. All embodiments of any aspect of the invention can be used in combination, unless the context clearly dictates otherwise.

As used herein, "about" means +/−5% of the recited value.

In one aspect, the present invention provides compositions, comprising particles including at least 95% by weight of a taxane, or a pharmaceutically acceptable salt thereof, wherein the particles have one or both of the following characteristics:

(i) a mean bulk density between about 0.050 g/cm$^3$ and about 0.15 g/cm$^3$, and/or (ii) have a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g.

The inventors have unexpectedly been able to produce compositions comprising the recited taxane particles that have a mean bulk density between about 0.050 g/cm$^3$ and about 0.15 g/cm$^3$, and/or a specific surface area (SSA) of at least 18 m$^2$/g an SSA using novel methods for producing the particles as described herein. As shown in the examples that follow, the increased specific surface area and decreased bulk density of the taxane particles result in significant increases in dissolution rate compared to the raw taxane and to milled taxane products used for comparison. Dissolution takes place only at a solid/liquid interface. Therefore, increased specific surface area will increase the dissolution rate due to a larger number of molecules on the surface of the particle having contact with the dissolution media. The bulk density takes into account the macrostructure and inter-particle space of a powder. Parameters that contribute to the bulk density include particle size distribution, particle shape, and the affinity of the particles for each other (i.e., agglomeration). Lower powder bulk densities yield faster dissolution rates. This is due to the ability of the dissolution media to more readily penetrate the interstitial or inter-particle spaces and have greater contact with the surface of the particles. Therefore, each of the increased specific surface area and the decreased bulk density result in the significant increase in dissolution rate for the taxane particles of the invention compared to the unprocessed or raw material, and the milled taxane product used for comparison. This provides a significant improvement for use of the taxane particles of the invention in, for example, tumor treatment.

As used herein, the "specific surface area" is the total surface area of the paclitaxel particle per unit of paclitaxel mass as measured by the Brunauer-Emmett-Teller ("BET") isotherm (i.e.: the BET SSA). As will be understood by those of skill in the art, the "taxane particles" include both agglomerated taxane particles and non-agglomerated taxane particles; since the SSA is determined on a per gram basis it takes into account both agglomerated and non-agglomerated taxane particles in the composition. The BET specific surface area test procedure is a compendial method included in both the United States Pharmaceopeia and the European Pharmaceopeia.

As used herein, the bulk density of the taxane particles is the mass of the totality of particles in the composition divided by the total volume they occupy when poured into a graduated cylinder. The total volume includes particle volume, inter-particle void volume, and internal pore volume.

Taxanes are a class of diterpenoids containing a taxadiene core that are very poorly soluble in water. The taxane particles of the invention may be any suitable taxane, including but not limited to paclitaxel, docetaxel, cabazitaxel, taxadiene, baccatin III, taxchinin A, brevifoliol, and taxuspine D, combinations thereof, or pharmaceutically acceptable salts thereof. In one embodiment, the taxane is selected from the group consisting of paclitaxel, docetaxel, and cabazitaxel, or a pharmaceutically acceptable salt thereof.

The "taxane particles" refers to particles of taxane that do not include an added excipient. Taxane particles are different than "particles containing taxane", which are particles that contain taxane and at least one added excipient. Taxane particles of the invention exclude a polymeric, wax or protein excipient and are not embedded, contained, enclosed or encapsulated within a solid excipient. Taxane particles of the invention may, however, contain impurities and byproducts typically found during preparation of taxane. Even so, taxane particles comprise at least 95%, at least 96%, at least 97%, at least 98%, at least 99% or 100% taxane, meaning the taxane particles consist of or consist essentially of substantially pure taxane. In one embodiment, the taxane particles are uncoated and exclude polymer, protein, polyethoxylated castor oil and polyethylene glycol glycerides composed of mono-, di- and triglycerides and mono- and diesters of polyethylene glycol.

The compositions of the invention have a mean particle size of between in the range of about 0.2 µm to about 5 µm, about 0.4 µm to about 3 µm or about 0.5 µm to about 1.4 µm. In a further embodiment, the compositions have a mean particle size of between about 0.4 µm and about 1.2 µm. In another embodiment the mean particle size is between about 0.4 µm and about 1.2 µm, or between about 0.6 µm and about 1.0 µm.

In one embodiment, the taxane is paclitaxel or a pharmaceutically acceptable salt thereof, and the particles have a mean bulk density between about 0.050 g/cm$^3$ and about 0.12 g/cm$^3$. In another embodiment, the paclitaxel particles have a mean bulk density between about 0.060 g/cm$^3$ and about 0.11 g/cm$^3$.

In a further embodiment, the taxane is paclitaxel or a pharmaceutically acceptable salt thereof, and wherein the paclitaxel particles have a specific surface area (SSA) of at least 18 m$^2$/g. In various further embodiments, the paclitaxel particles have a SSA of at least 20 m$^2$/g, 25 m$^2$/g, 30 m$^2$/g, 32 m$^2$/g, 34 m$^2$/g, or 35 m$^2$/g. In a further embodiment, the paclitaxel particles have a SSA of between about 22 m$^2$/g and about 40 m$^2$/g, between about 25 m$^2$/g and about 40 m$^2$/g, between about 30 m$^2$/g and about 40 m$^2$/g, or between about 35 m$^2$/g and about 40 m$^2$/g.

In one preferred embodiment, the paclitaxel particles have a mean bulk density of between about between about 0.050 g/cm$^3$ and about 0.12 g/cm$^3$ and a SSA of at least 30 m$^2$/g. In another preferred embodiment, the paclitaxel particles have a mean bulk density of between about between about 0.050 g/cm$^3$ and about 0.12 g/cm$^3$ and a SSA of at least 35 m$^2$/g. In one the paclitaxel particles have a mean bulk density of between about between about 0.050 g/cm$^3$ and about 0.12 g/cm$^3$ and a SSA of between about 30 m$^2$/g and about 40 m$^2$/g. In another preferred embodiment, the paclitaxel particles have a mean bulk density of between about 0.060 g/cm$^3$ and about 0.11 g/cm$^3$ and a SSA of between about 30 m$^2$/g and about 40 m$^2$/g. In another preferred embodiment, the paclitaxel particles have a mean bulk density of between about 0.060 g/cm$^3$ and about 0.11 g/cm$^3$ and a SSA of at least 30 m$^2$/g. In a further embodiment, the paclitaxel particles have a mean bulk density of between about 0.060 g/cm$^3$ and about 0.11 g/cm$^3$ and a SSA of at least 35 m$^2$/g. These various embodiments are exemplified in the examples that follow.

In any of these various embodiments, the paclitaxel particles may include at least $4.16 \times 10^{-13}$ gram paclitaxel, or a pharmaceutically acceptable salt thereof per paclitaxel particle.

In another embodiment, at least 40% (w/w) of the paclitaxel in the paclitaxel particles of the composition is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In another embodiment, the taxane is docetaxel or a pharmaceutically acceptable salt thereof, and the docetaxel particles have a mean bulk density between about 0.050 g/cm$^3$ and about 0.12 g/cm$^3$. In a further embodiment, the mean bulk density of the docetaxel particles is between about 0.06 g/cm$^3$ and about 0.1 g/cm$^3$.

In another embodiment, the taxane is docetaxel or a pharmaceutically acceptable salt thereof, and wherein the docetaxel particles have a SSA of at least 18 m$^2$/g. In various further embodiments, the docetaxel particles have a SSA of at least 20 m$^2$/g, 25 m$^2$/g, 30 m$^2$/g, 35 m$^2$/g, 40 m$^2$/g, or 42 m$^2$/g. In a further embodiment, the docetaxel particles have a SSA of between about 40 m$^2$/g and about 50 m$^2$/g. In another embodiment, the docetaxel particles have a SSA of between about 43 m$^2$/g and about 46 m$^2$/g.

In one preferred embodiment, the docetaxel particles have a mean bulk density between about 0.050 g/cm$^3$ and about 0.12 g/cm$^3$ and a SSA of at least 30 m$^2$/g. In another preferred embodiment, the docetaxel particles have a mean bulk density between about 0.050 g/cm$^3$ and about 0.12 g/cm$^3$ and a SSA of at least 35 m$^2$/g. In a further preferred embodiment, the docetaxel particles have a mean bulk density between about 0.050 g/cm$^3$ and about 0.12 g/cm$^3$ and a SSA of at least 40 m$^2$/g. In one preferred embodiment, the docetaxel particles have a mean bulk density between about 0.050 g/cm$^3$ and about 0.12 g/cm$^3$ and a SSA of between about 40 m$^2$/g and about 50 m$^2$/g. In another preferred embodiment, mean bulk density of the docetaxel particles is between about 0.06 g/cm$^3$ and about 0.1 g/cm$^3$ and the SSA is between about 40 m$^2$/g and about 50 m$^2$/g. These various embodiments are exemplified in the examples that follow.

In any of these various embodiments, the docetaxel particles may include at least $4.16 \times 10^{-13}$ grams docetaxel, or a pharmaceutically acceptable salt thereof per docetaxel particle.

In another embodiment, at least 20% (w/w) of the docetaxel is dissolved in 30 minutes or less in a solution of 15% methanol/85% water (v/v) in a USP II paddle apparatus operating at 75 RPM. A neutral pH was used where the solubility of the taxanes are not effected by pH. In another embodiment, the dissolution studies are carried out at 37° C.

In a further aspect, the invention provides compositions comprising particles including at least 95% by weight of paclitaxel, or a pharmaceutically acceptable salt thereof, wherein the particles have a specific surface area (SSA) of at least 12 $m^2/g$. In various embodiments, the paclitaxel particles have an SSA of at least 12, 13, 14, 15, 16, 17, 18, 19, 20, 21, 22, 23, 24, 25, 26, 27, 28, 29, 30, 31, 32, 33, 34, 35, 36, 37, 38, 39, or 40 $m^2/g$. In various further embodiments, the paclitaxel particles have an SSA of between about 12 $m^2/g$ and about 40 $m^2/g$, about 14 $m^2/g$ and about 40 $m^2/g$, about 15 $m^2/g$ and about 40 $m^2/g$, about 16 $m^2/g$ and about 40 $m^2/g$, about 17 $m^2/g$ and about 40 $m^2/g$, about 18 $m^2/g$ and about 40 $m^2/g$, about 19 $m^2/g$ and about 40 $m^2/g$, about 20 $m^2/g$ and about 40 $m^2/g$, about 22 $m^2/g$ and about 40 $m^2/g$, about 26 $m^2/g$ and about 40 $m^2/g$, about 30 $m^2/g$ and about 40 $m^2/g$, between about 20 $m^2/g$ and about 29 $m^2/g$, between about 20 $m^2/g$ and about 28 $m^2/g$, between about 20 $m^2/g$ and about 26.2 $m^2/g$, between about 22 $m^2/g$ and about 29 $m^2/g$, between about 22 $m^2/g$ and about 28 $m^2/g$, between about 22 $m^2/g$ and about 26.2 $m^2/g$, between about 32 $m^2/g$ and about 39 $m^2/g$, between about 32 $m^2/g$ and about 38.5 $m^2/g$, between about 32 $m^2/g$ and about 35 $m^2/g$, between about 35 $m^2/g$ and about 40 $m^2/g$, and between about 35 $m^2/g$ and about 38.5 $m^2/g$. In other embodiments, the paclitaxel particles have an SSA of:

(a) between 16 $m^2/g$ and 31 $m^2/g$ or between 32 $m^2/g$ and 40 $m^2/g$;
(b) between 16 $m^2/g$ and 30 $m^2/g$ or between 32 $m^2/g$ and 40 $m^2/g$;
(c) between 16 $m^2/g$ and 29 $m^2/g$ or between 32 $m^2/g$ and 40 $m^2/g$;
(d) between 17 $m^2/g$ and 31 $m^2/g$ or between 32 $m^2/g$ and 40 $m^2/g$;
(e) between 17 $m^2/g$ and 30 $m^2/g$ or between 32 $m^2/g$ and 40 $m^2/g$;
(f) between 17 $m^2/g$ and 29 $m^2/g$, or between 32 $m^2/g$ and 40 $m^2/g$;
(g) between 16 $m^2/g$ and 31 $m^2/g$ or between 33 $m^2/g$ and 40 $m^2/g$;
(h) between 16 $m^2/g$ and 30 $m^2/g$ or between 33 $m^2/g$ and 40 $m^2/g$;
(i) between 16 $m^2/g$ and 29 $m^2/g$ or between 33 $m^2/g$ and 40 $m^2/g$;
(j) between 17 $m^2/g$ and 31 $m^2/g$ or between 33 $m^2/g$ and 40 $m^2/g$;
(k) between 17 $m^2/g$ and 30 $m^2/g$ or between 33 $m^2/g$ and 40 $m^2/g$;
(l) between 17 $m^2/g$ and 29 $m^2/g$, or between 33 $m^2/g$ and 40 $m^2/g$;
(m) between 16 $m^2/g$ and 31 $m^2/g$, or 32 $m^2/g$;
(h) between 17 $m^2/g$ and 31 $m^2/g$, or 32 $m^2/g$;
(i) between 16 $m^2/g$ and 30 $m^2/g$, or 32 $m^2/g$;
(j) between 17 $m^2/g$ and 30 $m^2/g$, or 32 $m^2/g$;
(k) between 16 $m^2/g$ and 29 $m^2/g$, or 32 $m^2/g$;
(l) between 17 $m^2/g$ and 29 $m^2/g$, or 32 $m^2/g$;
(m) between 16 $m^2/g$ and 31 $m^2/g$, or 33 $m^2/g$;
(n) between 17 $m^2/g$ and 31 $m^2/g$, or 33 $m^2/g$;
(o) between 16 $m^2/g$ and 30 $m^2/g$, or 33 $m^2/g$;
(p) between 17 $m^2/g$ and 30 $m^2/g$, or 33 $m^2/g$;
(q) between 16 $m^2/g$ and 29 $m^2/g$, or 33 $m^2/g$; or
(r) between 17 $m^2/g$ and 29 $m^2/g$, or 33 $m^2/g$.

In another embodiment, at least 40% (w/w) of the paclitaxel in the paclitaxel particles of the composition is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In another aspect, the present invention provides compositions, comprising particles including at least 95% by weight of paclitaxel, wherein at least 40% (w/w) of the paclitaxel is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In a further aspect, the present invention provides composition, comprising including at least 95% by weight of docetaxel, wherein at least 20% (w/w) of the docetaxel is dissolved in 30 minutes or less in a solution of 15% methanol/85% water (v/v) in a USP II paddle apparatus operating at 75 RPM. pH 7 was used, and the solubility of the taxanes are not effected by pH. In another embodiment, the dissolution studies are carried out at 37° C.

In a further embodiment, the composition comprises a suspension further comprising a pharmaceutically acceptable aqueous carrier. The suspension of the invention comprises taxane particles and a liquid carrier. The liquid carrier can be aqueous. The suspension excludes a solid excipient within which the paclitaxel is contained and excludes GELUCIRE® (polyethylene glycol glycerides composed of mono-, di- and triglycerides and mono- and diesters of polyethylene glycol), and CREMOPHOR® (polyethoxylated castor oil).

Even though the paclitaxel particles do not include an added excipient, the liquid carrier of the suspension can comprise water and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise taxane particles, water, buffer and salt. It optionally further comprises a surfactant. In some embodiments, the suspension consists essentially of or consists of water, taxane particles suspended in the water and buffer. The suspension can further contain an osmotic salt.

The suspension can comprise one or more surfactants. Suitable surfactants include by way of example and without limitation polysorbates, lauryl sulfates, acetylated monoglycerides, diacetylated monoglycerides, and poloxamers.

The suspension can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

In one embodiment especially suitable for intraperitoneal (IP) administration, the suspension may be formulated to be hyperosmolar (hypertonic), hypomolar (hypotonic) or isosmolar (isotonic) with respect to the fluid(s) of the IP cavity. In some embodiments, the suspension may be isotonic with respect to fluid in the IP cavity. In such an embodiment, the he osmolality of the suspension can range from about 200 to about 380, about 240 to about 340, about 280 to about 300 or about 290 mOsm/kg.

The suspension can comprise one or more buffering agents. Suitable buffering agents include by way of example and without limitation, dibasic sodium phosphate, monobasic sodium phosphate, citric acid, sodium citrate hydrochloric acid, sodium hydroxide, tris(hydroxymethyl)aminomethane, bis(2-hydroxyethyl)iminotris-(hydroxymethyl)methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The suspension can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, polysorbate 80, and propylene glycol; polyvinyl alcohol from about 0.1 to about 4%; povidone from about 0.1 to about 2%; and dextran 70 from about 0.1% when used with another polymeric demulcent described herein.

The suspension can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art The suspension can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The suspension can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE®, octoxynol and others known to those of ordinary skill in the art.

The suspension can comprise one or more viscosity modifiers that increase or decrease the viscosity of the suspension. Suitable viscosity modifiers include methylcellulose, hydroxypropyl methycellulose, mannitol and polyvinylpyrrolidone.

The suspension can comprise one or more osmotic agents such as those used for peritoneal dialysis. Suitable osmotic agents include icodextrin (a glucose polymer), sodium chloride, potassium chloride, and salts that are also used as buffering agents.

As used herein, "pharmaceutically acceptable salts" of the taxanes are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the taxanes. The term "salts" refers to the relatively non-toxic, inorganic and organic acid addition salts of taxanes. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.)

In one embodiment, the composition comprises a dosage form of taxane in suspension (i.e.: with a pharmaceutically acceptable carrier and any other components), in a dosage deemed suitable by an attending physician for an intended use. Any suitable dosage form may be used; in various non-limiting embodiments, the dosage form is adequate to provide about 0.01 mg/kg to about 50 mg/kg of body weight per day. In various further embodiments, the dosage form is adequate to provide about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg of body weight per day. The suspension can be administered as is or can be diluted with a diluent, e.g. with saline water for injection optionally including a buffering agent and one or more other excipients, prior to administration. For example, the volume ratio of suspension to diluent might be in the range of 1:1-1:100 (v/v) or other suitable ratio.

In another aspect, the invention provides methods for treating a tumor, comprising administering to a subject with a tumor an amount effective to treat the tumor of the composition or suspension of any embodiment or combination of embodiments of the invention. The inventors have unexpectedly been able to produce compositions comprising the recited taxane particles that have a mean bulk density between about 0.050 g/cm$^3$ and about 0.15 g/cm$^3$, and/or a specific surface area (SSA) of at least 18 m$^2$/g an SSA using novel methods for producing the particles as described herein. Each of the increased specific surface area and the decreased bulk density result in the significant increase in dissolution rate for the taxane particles of the invention compared to the unprocessed or raw material, and the milled taxane product used for comparison. This provides a significant improvement for use of the taxane particles of the invention in, for example, tumor treatment.

As used herein, a "tumor" includes benign tumors, premalignant tumors, malignant tumors that have not metastasized, and malignant tumors that have metastasized.

The methods of the invention can be used to treat tumor that is susceptible to taxane treatment, including but not limited to breast tumors, ovarian tumors, lung tumors, bladder tumors, prostate tumors, bone tumors, stomach tumors and pancreatic tumors. In one non-limiting embodiment, the tumor is located in whole or in part in the intraperitoneal cavity.

The subject may be any suitable subject with a tumor, including but not limited to humans, primates, dogs, cats, horses, cattle, etc.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Amounts effective for these uses depend on factors including, but not limited to, the nature of the taxane (specific activity, etc.), the route of administration, the stage and severity of the disorder, the weight and general state of health of the subject, and the judgment of the prescribing physician. It will be understood that the amount of the composition of suspension of the invention actually administered will be determined by a physician, in the light of the above relevant circumstances. In one non-limiting embodiment, an amount effective is an amount that provides between 0.01 mg/kg to about 50 mg/kg of body weight per day.

The compositions may be administered via any suitable route, including but not limited to orally, pulmonary, intraperitoneally, subcutaneous injection, intramuscular injection, or any other form of injection, as deemed most appropriate by attending medical personnel in light of all factors for a given subject. In one embodiment, the composition or suspension is administered intraperitoneally, for example, when the tumor is located (at least in part) in the peritoneal cavity. In this embodiment, the composition or suspension may be administered, for example, by perfusion or as a bolus into the peritoneal cavity. In a further embodiment, the administering may be initiated after removal of ascites fluid from the peritoneal cavity.

A dosing period is that period of time during which a dose of taxane particles in the composition or suspension is administered. The dosing period can be a single period of time during which the entire dose is administered, or it can be divided into two or more periods of time during each of which a portion of the dose is administered.

A post-dosing period is that period of time beginning after completion of a prior dosing period and ending after initiating a subsequent dosing period. The duration of the post-dosing period may vary according to a subject's clinical response to the paclitaxel. The suspension is not administered during the post-dosing period. A post-dosing period can last at least 7 days, at least 14 days, at least 21 days, at least 28 days, at least 35 days, at least 60 days or at least 90 days or longer. The post-dosing period can be kept constant for a subject or two or more different post-dosing periods can be used for a subject.

A dosing cycle includes a dosing period and a post-dosing period. Accordingly, the duration of a dosing cycle will be the sum of the dosing period and the post-dosing period. The dosing cycle can be kept constant for a subject or two or more different dosing cycles can be used for a subject.

In one embodiment, the administering is carried out more than once, and wherein each administration is separated in time by at least 21 days.

In another aspect, the invention provides methods for making compound particles, comprising:

(a) introducing (i) a solution comprising at least one solvent and at least one solute comprising a compound of interest into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% of the total power that can be generated using the sonic energy source during the passing, and wherein the nozzle orifice has a diameter of between 20 µm and 125 µm;

(c) contacting the atomized droplets with the compressed fluid, to cause depletion of the solvent from the atomized droplets, to produce compound particles;

wherein steps (a), (b), and (c) are carried out under supercritical temperature and pressure for the compressed fluid.

The methods of the invention involve contacting a solution, including a solvent with at least one compound of interest (including but not limited to an active pharmaceutical ingredient, such as a taxane) dispersed in the solvent, with a compressed fluid at supercritical conditions for the compressed fluid, so as to cause the compressed fluid to deplete the solvent and precipitate the compound away as extremely small particles.

The methods of the present invention provide a significant improvement over methods such as those disclosed in U.S. Pat. Nos. 5,833,891; 5,874,029; 6,113,795; and 8,778,181 (incorporated herein by reference in their entirety) using a compressed fluid in combination with appropriate solvents to reproducibly precipitate compounds as fine particles that have a narrow size distribution. The methods of the present invention are capable of producing the particles of the invention with significantly improved bulk density, SSA, and dissolution properties, and thus significantly improved therapeutic benefits. The methods provide this significant improvement, at least in part, through use of the sonic energy source external to the nozzle and at the recited distance from the nozzle orifice to provide significantly enhanced sonic energy and enhanced disruption of the solvent-solute flow as it exits the nozzle compared to the methods disclosed U.S. Pat. Nos. 5,833,891 and 5,874,029 that use a converging-diverging nozzle to create the sonic energy.

In one embodiment, the methods further comprise:
(d) contacting the atomized droplets produced in step (c) with an anti-solvent to cause further depletion of the solvent from the compound particles, wherein step (d) is carried out under supercritical temperature and pressure for the anti-solvent.

The methods of the invention utilize a sonic energy source located directly in the output stream of the solute dissolved in the solvent. Any suitable source of sonic energy may be used that is compatible with the methods of the invention, including but not limited to sonic horn, a sonic probe, or a sonic plate. In various embodiments, the nozzle orifice is located between about 2 mm and about 20 mm, about 2 mm and about 18 mm, about 2 mm and about 16 mm, about 2 mm and about 14 mm, about 2 mm and about 12 mm, about 2 mm and about 10 mm, about 2 mm and about 8 mm, about 2 mm and about 6 mm, about 2 mm and about 4 mm, about 4 mm and about 20 mm, about 4 mm and about 18 mm, about 4 mm and about 16 mm, about 4 mm and about 14 mm, about 4 mm and about 12 mm, about 4 mm and about 10 mm, about 4 mm and about 8 mm, about 4 mm and about 6 mm, about 6 mm and about 20 mm, about 6 mm and about 18 mm, about 6 mm and about 16 mm, about 6 mm and about 14 mm, about 6 mm and about 12 mm, about 6 mm and about 10 mm, about 6 mm and about 8 mm, about 8 mm and about 20 mm, about 8 mm and about 18 mm, about 8 mm and about 16 mm, about 8 mm and about 14 mm, about 8 mm and about 12 mm, about 8 mm and about 10 mm, about 10 mm and about 20 mm, about 10 mm and about 18 mm, about 10 mm and about 16 mm, about 10 mm and about 14 mm, about 10 mm and about 12 mm, about 12 mm and about 20 mm, about 12 mm and about 18 mm, about 12 mm and about 16 mm, about 12 mm and about 14 mm, about 14 mm and about 20 mm, about 14 mm and about 18 mm, about 14 mm and about 16 mm, about 16 mm and about 20 mm, about 16 mm and about 18 mm, and about 18 mm and about 20 mm, from the sonic energy source.

Figure 3:
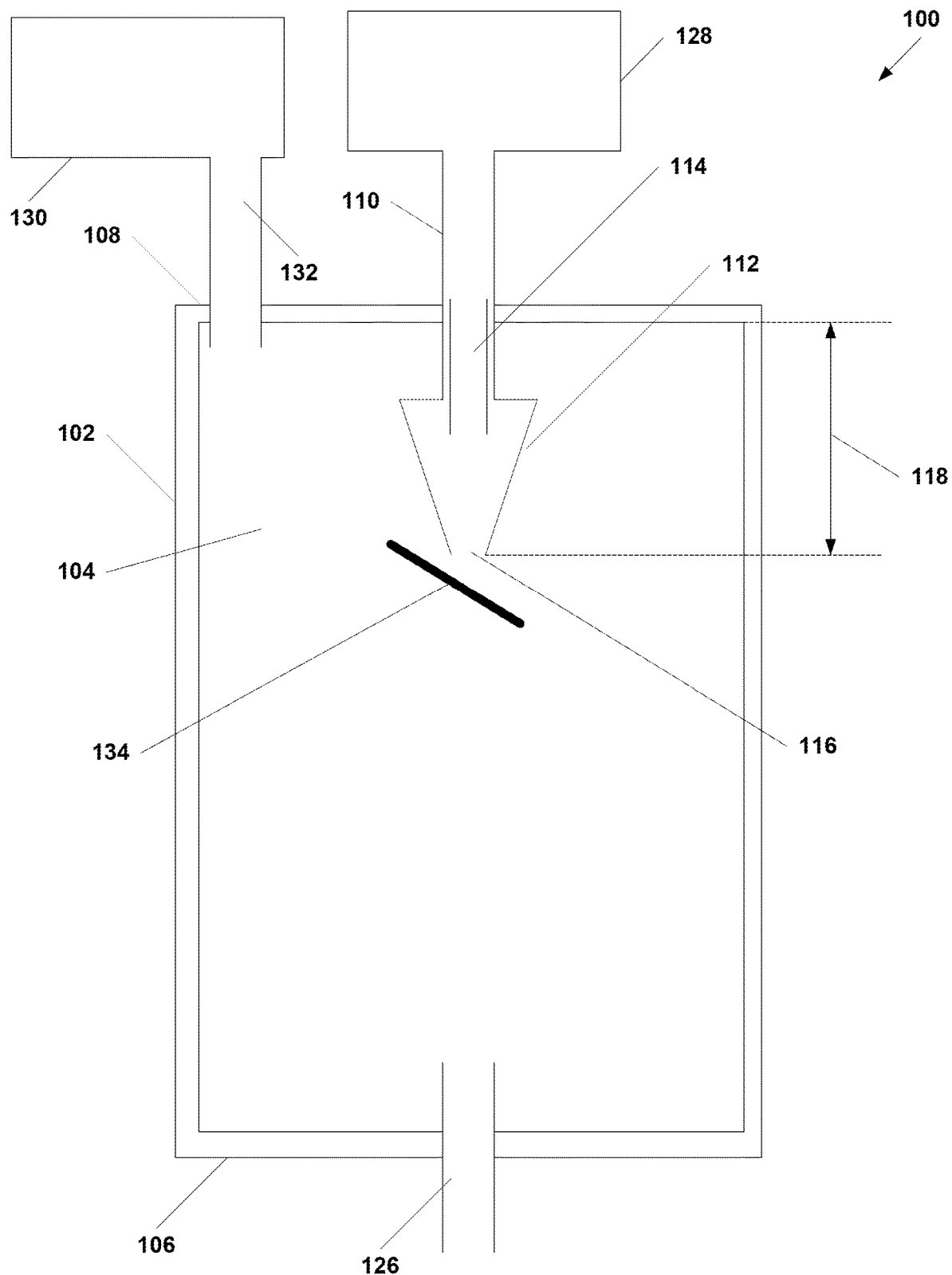
FIG. 3 illustrates a cross-section view of an example nozzle assembly, according to an example embodiment.

In further embodiments, with reference to the Figures, as shown in FIG. 3, the nozzle assembly 100 includes a vessel 102 defining a pressurizable chamber 104. The vessel 102 includes a distal end 106 and a proximal end 108. The nozzle assembly 100 further includes an inlet 110 of the pressurizable chamber 104 at the proximal end 108 of the vessel 102. The nozzle assembly 100 further includes a nozzle 112 positioned within the pressurizable chamber 104. As shown in FIG. 3, the nozzle 112 includes an inlet tube 114 in fluid communication with the inlet 110 of the pressurizable chamber 104. In addition, the nozzle 112 includes an outlet aperture 116. Further, as shown in FIG. 3, the nozzle 112 is adjustable to alter a distance 118 between the proximal end 108 of the vessel 102 and the outlet aperture 116 of the nozzle 112. As shown in FIG. 3, the nozzle 112 is further adjustable to alter an angle 120 between a longitudinal axis of the vessel 122 and a longitudinal axis of the nozzle 124. In addition, the nozzle assembly 100 includes an outlet 126 of the pressurizable chamber 104 at the distal end 106 of the vessel 102.

The nozzle assembly 100 may further include a first reservoir 128 and a second reservoir 130. The first reservoir 128 may include a supply of solvent, while the second reservoir 130 may include a supply of anti-solvent. The inlet 110 of the pressurizable chamber 104 may be in fluid communication with the first reservoir 128, and a second inlet 132 of the pressurizable chamber 104 may be in fluid communication with the second reservoir 130. In one example, the first reservoir 128 is in fluid communication with the inlet tube 114 of the nozzle 112, such that the solvent enters the pressurizable chamber 104 through the nozzle 112. Other examples are possible as well.

The outlet aperture 116 of the nozzle 112 may include a plurality of ridges to create a vortex within the nozzle 112 such that the solvent exits the nozzle 112 via turbulent flow. In another example, the nozzle 112 may include a porous frit interior to the nozzle 112 such that the solvent exits the nozzle 112 via turbulent flow. In yet another example, the outlet aperture 116 of the nozzle 112 may have a small diameter (as discussed in additional detail below) such that the solvent exits the nozzle 112 via turbulent flow. These various embodiments that cause turbulent flow may assist in mixing the solvent with the anti-solvent within the pressurizable chamber 104. Further, the inlet tube 114 of the nozzle 112 may have an inner diameter with a range from about 1.5875 mm to about 6.35 mm. In one example, both the angle of the nozzle 112 and the vertical position of the nozzle 112 may be adjusted manually by a user. For example, the nozzle 112 may be positioned on a vertical support that can be adjusted to alter the distance 118 between the proximal end 108 of the vessel 102 and the outlet aperture 116 of the nozzle 112. Further, the nozzle 112 may be rotated manually to adjust the angle 120 between the longitudinal axis of the vessel 122 and the longitudinal axis of the nozzle 124. In another example, the nozzle assembly 100 may include a motor coupled to the nozzle 112. In various examples, the motor may be configured to alter the distance 118 between the proximal end 108 of the vessel 102 and the outlet aperture 116 of the nozzle 112 and/or alter the angle 120 between the longitudinal axis of the vessel 122 and the longitudinal axis of the nozzle 124. Such a motor may be an electric motor powered by electrical power, or may be powered by a number of different energy sources, such as a gas-based fuel or solar power. The motor may be coupled directly or indirectly to the nozzle 112, such that when the motor is turned on the distance 118 between the proximal end 108 of the vessel 102 and the outlet aperture 116 of the nozzle 112 increases or decreases depending on the direction the motor rotates. The motor may be coupled to a series of gears that adjusts the distance 118 between the proximal end 108 of the vessel 102 and the outlet aperture 116 of the nozzle 112 and/or adjusts the angle 120 between the longitudinal axis of the vessel 122 and the longitudinal axis of the nozzle 124, or the motor may be coupled to a pulley system that adjusts the distance 118 between the proximal end 108 of the vessel 102 and the outlet aperture 116 of the nozzle 112 and/or adjusts the angle 120 between the longitudinal axis of the vessel 122 and the longitudinal axis of the nozzle 124. Other configurations are possible as well.

In another example, the nozzle 112 assembly may include an actuator coupled to the nozzle 112, where the actuator alters the distance 118 between the proximal end 108 of the vessel 120 and the outlet aperture 116 of the nozzle 112 and/or alters the angle 120 between the longitudinal axis of the vessel 122 and the longitudinal axis of the nozzle 124. Such an actuator may be an electro-mechanical actuator, including an electric motor that converts a rotary motion of the electric motor to a linear displacement via a linkage system. Other potential actuators are possible as well, such as hydraulic actuators, pneumatic actuators, piezoelectric actuators, linear motors, or telescoping linear actuators, as examples.

Figure 4:
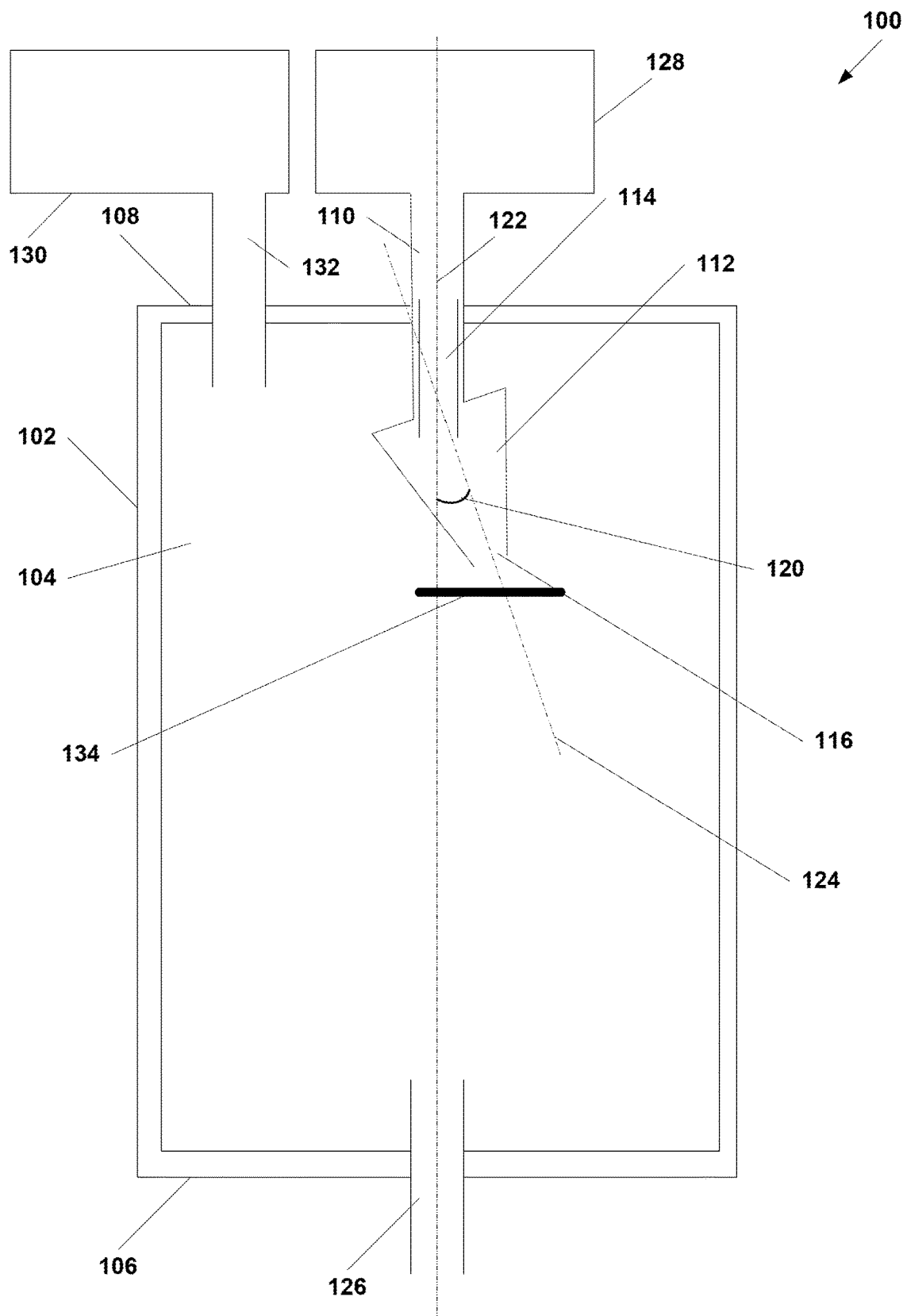
FIG. 4 illustrates a cross-section view of another example nozzle assembly, according to an example embodiment.

In one example, as shown in FIGS. 3 and 4, the nozzle assembly further includes a sonic energy source 134 positioned adjacent to the outlet aperture 116 of the nozzle 112. In one example, the sonic energy source 134 may include a sonic probe extending within the pressurizable chamber 104. In another example, the sonic energy source 134 may include a sonic surface positioned in the pressurizable chamber 104. The sonic waves from the sonic energy source 134 cause the liquids in the pressurizable chamber 104 to shatter, thereby enhancing mixing of the solvent and anti-solvent solutions to create particles within the pressurizable chamber 104. In one example, the sonic energy source 134 is positioned at an angle of 45 degrees with respect to the longitudinal axis of the nozzle 124. Other angles are possible as well. In one example, the sonic energy source 134 may be adjustable to alter a distance between the outlet aperture 116 of the nozzle 112 and the sonic energy source 134. Further, the sonic energy source 134 may be adjustable to alter an angle between the sonic energy source 134 and the longitudinal axis of the nozzle 124.

Any suitable source of sonic energy may be used that is compatible with the methods of the invention, including but not limited to sonic horn, a sonic probe, or a sonic plate. In various further embodiments, the sonic energy source produces sonic energy with an amplitude between about 1% and about 100% of the total power that can be generated using the sonic energy source. In light of the teachings herein, one of skill in the art can determine an appropriate sonic energy source having a specific total power output to be used. In one embodiment, the sonic energy source has a total power output of between about 500 and about 900 watts; in various further embodiments, between about 600 and about 800 watts, about 650-750 watts, or about 700 watts.

In various further embodiments, the sonic energy source produces sonic energy with a power output between about 5% and about 100%, about 10% and about 100%, 20% and about 100%, about 30% and about 100%, about 40% and about 100%, about 50% and about 100%, about 60% and about 100%, about 70% and about 100%, about 80% and about 100%, about 90% and about 100%, about 1% and about 90%, about 5% and about 90%, about 10% and about 90%, about 20% and about 90%, about 30% and about 90%, about 40% and about 90%, about 50% and about 90%, about 60% and about 90%, about 70% and about 90%, about 80% and about 90%, about 1% and about 80%, about 5% and about 80%, about 10% and about 80%, about 20% and about 80%, about 30% and about 80%, about 40% and about 80%, about 50% and about 80%, about 60% and about 80%, about 70% and about 80%, about 1% and about 70%, about 5% and about 70%, about 10% and about 70%, about 20% and about 70%, about 30% and about 70%, about 40% and about 70%, about 50% and about 70%, about 60% and about 70%, about 1% and about 60%, about 5% and about 60%, about 10% and about 60%, about 20% and about 60%, about 30% and about 60%, about 40% and about 60%, about 50% and about 60%, about 1% and about 50%, about 5% and about 50%, about 10% and about 50%, about 20% and about 50%, about 30% and about 50%, about 40% and about 50%, about 1% and about 40%, about 5% and about 40%, about 10% and about 40%, about 20% and about 40%, about 30% and about 40%, about 1% and about 30%, about 5% and about 30%, about 10% and about 30%, about 20% and about 30%, about 1% and about 20%, about 5% and about 20%, about 10% and about 20%, about 1%, 5%, 10%, 20%, 30%, 40%, 50%, 60%, 70%, 80%, 90%, or about 100% of the total power that can be generated using the sonic energy source. In various embodiments, the sonic energy source produces sonic energy with power output of about 1%-80%, 20-80%, 30-70%, 40-60%, or about 60% of the total power that can be generated using the sonic energy source. In light of the teachings herein, one of skill in the art can determine an appropriate frequency to be utilized on the sonic energy source. In one embodiment, a frequency of between about 18 and about 22 kHz on the sonic energy source is utilized. In various other embodiments, a frequency of between about 19 and about 21 kHz, about 19.5 and about 20.5, or a frequency of about 20 kHz on the sonic energy source is utilized.

In various further embodiments, the nozzle orifice has a diameter of between about 20 µm and about 125 µm, about 20 µm and about 115 µm, about 20 µm and about 100 µm, about 20 µm and about 90 µm, about 20 µm and about 80 µm, about 20 µm and about 70 µm, about 20 µm and about 60 µm, about 20 µm and about 50 µm, about 20 µm and about 40 µm, about 20 µm and about 30 µm, between about 30 µm and about 125 µm, about 30 µm and about 115 µm, about 30 µm and about 100 µm, about 30 µm and about 90 µm, about 30 µm and about 80 µm, about 30 µm and about 70 µm, about 30 µm and about 60 µm, about 30 µm and about 50 µm, about 30 µm and about 40 µm, between about 40 µm and about 125 µm, about 40 µm and about 115 µm, about 40 µm and about 100 µm, about 40 µm and about 90 µm, about 40 µm and about 80 µm, about 40 µm and about 70 µm, about 40 µm and about 60 µm, about 40 µm and about 50 µm, between about 50 µm and about 125 µm, about 50 µm and about 115 µm, about 50 µm and about 100 µm, about 50 µm and about 90 µm, about 50 µm and about 80 µm, about 50 µm and about 70 µm, about 50 µm and about 60 µm, between about 60 µm and about 125 µm, about 60 µm and about 115 µm, about 60 µm and about 100 µm, about 60 µm and about 90 µm, about 60 µm and about 80 µm, about 60 µm and about 70 µm, between about 70 µm and about 125 µm, about 70 µm and about 115 µm, about 70 µm and about 100 µm, about 70 µm and about 90 µm, about 70 µm and about 80 µm, between about 80 µm and about 125 µm, about 80 µm and about 115 µm, about 80 µm and about 100 µm, about 80 µm and about 90 µm, between about 90 µm and about 125 µm, about 90 µm and about 115 µm, about 90 µm and about 100 µm, between about 100 µm and about 125 µm, about 100 µm and about 115 µm, between about 115 µm and about 125 µm, about 20 µm, 30 µm, 40 µm, 50 µm, 60 µm, 70 µm, 80 µm, 90 µm, 100 µm, 115 µm, or about 120 µm. The nozzle is inert to both the solvent and the compressed fluid used in the methods.

In further examples, the system may include a plurality of nozzles, with each nozzle positioned at a different angle between a longitudinal axis of the vessel and a longitudinal axis of the nozzle and/or a different distance between the nozzle orifice and the sonic energy source. A given nozzle of the plurality of nozzles may be chosen for a given production run to produce a certain type of particle having a given SSA.

Any suitable solvent and solute may be used; exemplary such solutes and solvents are disclosed in U.S. Pat. Nos. 5,833,891 and 5,874,029. In one non-limiting embodiment, the solute/compound comprises a taxane, including those discussed herein. In various other non-limiting embodiments, the solvent may comprise acetone, ethanol, methanol, dichloromethane, ethyl acetate, chloroform, acetonitrile, and suitable combinations thereof. In one embodiment, the solute/compound is paclitaxel and the solvent is acetone. In another embodiment, the solute/compound is docetaxel and the solvent is ethanol. The solvents should comprise at least about 80%, 85%, or 90% by weight of the overall solution.

The compressed fluid is capable of forming a supercritical fluid under the conditions used, and the solute that forms the particles is poorly soluble or insoluble in the compressed fluid. As is known to those of skill in the art, a supercritical fluid is any substance at a temperature and pressure above its critical point, where distinct liquid and gas phases do not exist. Steps (a), (b), and (c) of the methods of the invention are carried out under supercritical temperature and pressure for the compressed fluid, such that the compressed fluid is present as a supercritical fluid during these processing steps.

The compressed fluid can serve as a solvent for and can be used to remove unwanted components in the particles. Any suitable compressed fluid may be used in the methods of the invention; exemplary such compressed fluids are disclosed in U.S. Pat. Nos. 5,833,891 and 5,874,029. In one non-limiting embodiment, suitable supercritical fluid-forming compressed fluids and/or anti-solvents can comprise carbon dioxide, ethane, propane, butane, isobutane, nitrous oxide, xenon, sulfur hexafluoride and trifluoromethane. The anti-solvent recited in step (d) to cause further solvent depletion, is a compressed fluid as defined above, and may be the same compressed fluid used in steps (a-c), or may be different. In one embodiment, the anti-solvent used in step (d) is the same as the compressed fluid used in steps (a-c).

In a preferred embodiment, the compressed fluid and the anti-solvent are both super-critical carbon dioxide.

In all cases, the compressed fluid and anti-solvent should be substantially miscible with the solvent while the compound to be precipitated should be substantially insoluble in the compressed fluid, i.e., the compound, at the selected solvent/compressed fluid contacting conditions, should be no more than about 5% by weight soluble in the compressed fluid or anti-solvent, and preferably is essentially completely insoluble.

The supercritical conditions used in the methods of the invention are typically in the range of from 1× to about 1.4×, or 1× to about 1.2× of the critical temperature of the supercritical fluid, and from 1× to about 7×, or 1× to about 2×, of the of the supercritical pressure for the compressed fluid.

It is well within the level of those of skill in the art to determine the critical temperature and pressure for a given compressed fluid or anti-solvent. In one embodiment, the compressed fluid and anti-solvent are both super critical carbon dioxide, and the critical temperature is at least 31.1° C. and up to about 60° C., and the critical pressure is at least 1071 psi and up to about 1800 psi. In another embodiment, the compressed fluid and anti-solvent are both super critical carbon dioxide, and the critical temperature is at least 35° C. and up to about 55° C., and the critical pressure is at least 1070 psi and up to about 1500 psi. It will be understood by those of skill in the art that the specific critical temperature and pressure may be different at different steps during the processing.

Any suitable pressurizable chamber may be used, including but not limited to those disclosed in U.S. Pat. Nos. 5,833,891 and 5,874,029. Similarly, the steps of contacting the atomized droplets with the compressed fluid to cause depletion of the solvent from the droplets; and contacting the droplets with an anti-solvent to cause further depletion of the solvent from the droplets, to produce particles of the compound can be carried out under any suitable conditions, including but not limited to those disclosed in U.S. Pat. Nos. 5,833,891 and 5,874,029.

The flow rate can be adjusted as high as possible to optimize output but below the pressure limitations for the equipment, including the nozzle orifice. In one embodiment, the flow rate of the solution through the nozzle has a range from about 0.5 mL/min to about 30 mL/min. In various further embodiments, the flow rate is between about 0.5 mL/min to about 25 mL/min, 0.5 mL/min to about 20 mL/min, 0.5 mL/min to about 15 mL/min, 0.5 mL/min to about 10 mL/min, 0.5 mL/min to about 4 mL/min, about 1 mL/min to about 30 mL/min, about 1 mL/min to about 25 mL/min, about 1 mL/min to about 20 mL/min, 1 mL/min to about 15 mL/min, about 1 mL/min to about 10 mL/min, about 2 mL/min to about 30 mL/min, about 2 mL/min to about 25 mL/min, about 2 mL/min to about 20 mL/min, about 2 mL/min to about 15 mL/min, or about 2 mL/min to about 10 mL/min. The solution of drug subject to the flow rate can be any suitable concentration, such as between about 1 mg/ml and about 80 mg/ml.

In one embodiment, the methods further comprise receiving the plurality of particles through the outlet of the pressurizable chamber; and collecting the plurality of particles in a collection device.

Figure 8:
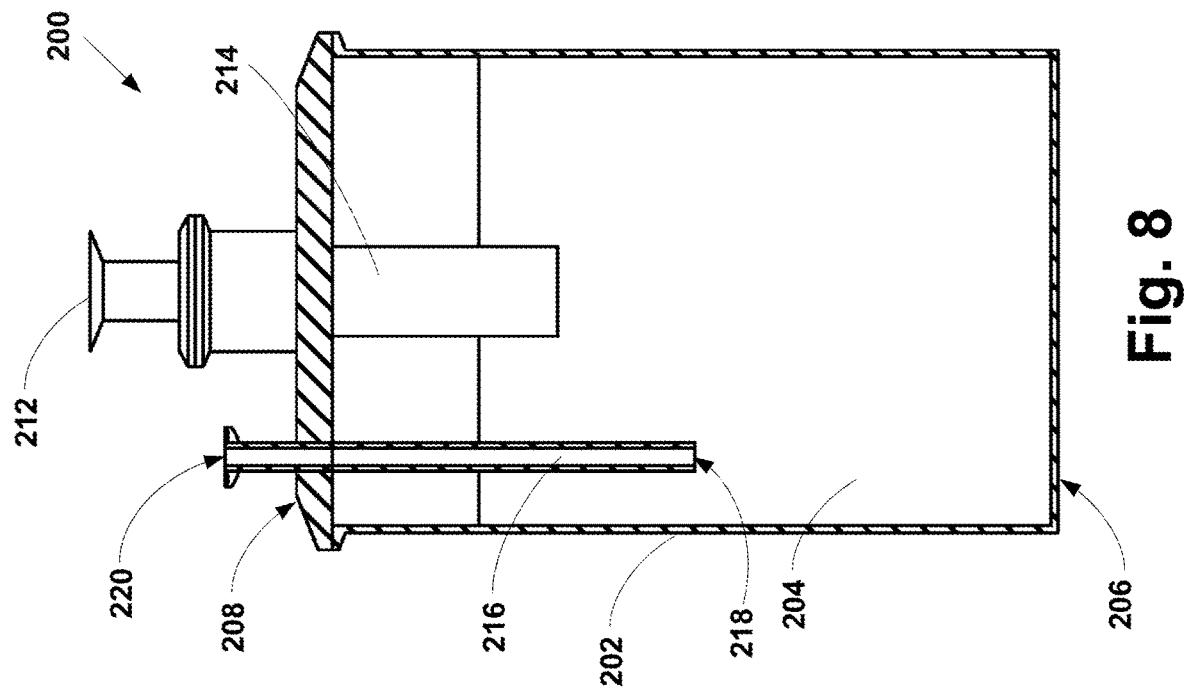
FIG. 8 illustrates another cross-section view of the particle collection device, according to an example embodiment.
Figure 7:
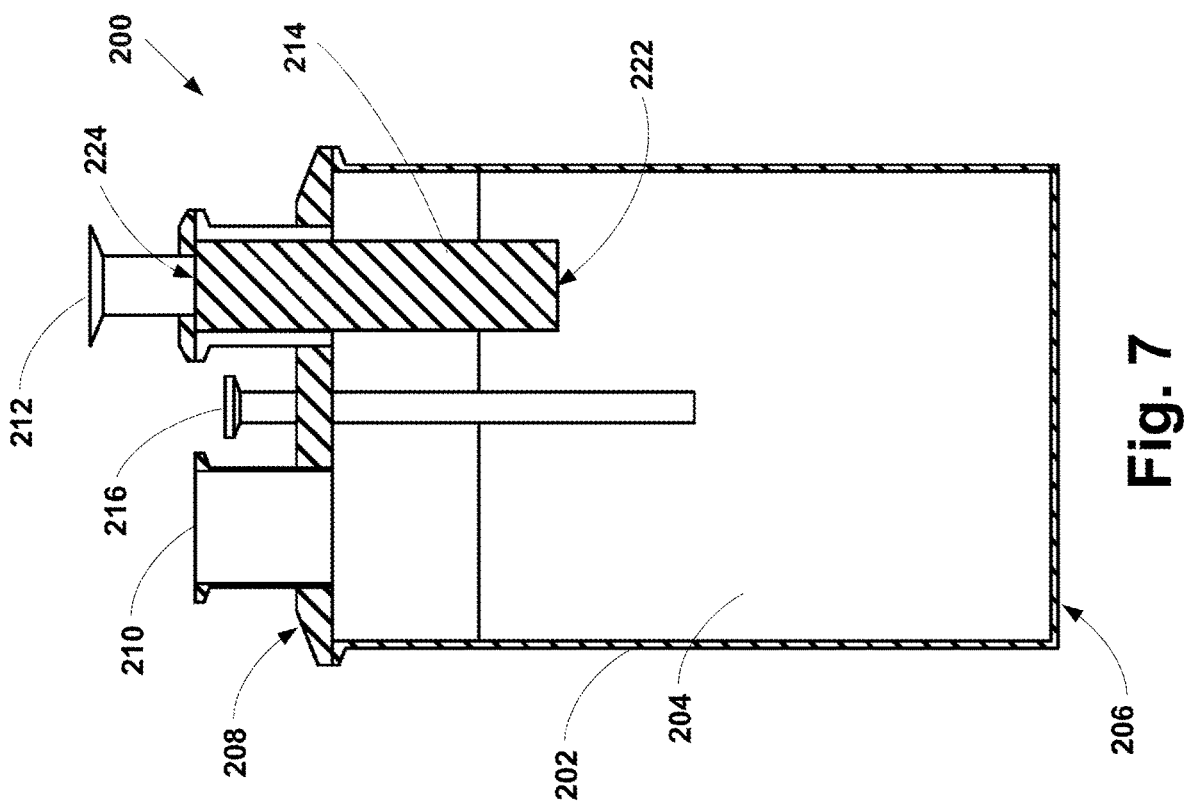
FIG. 7 illustrates a cross-section view of the particle collection device, according to an example embodiment.

In such an embodiment, with reference to the Figures, as shown in FIG. 5, the invention comprises a collection device 200 including a vessel 202 defining a chamber 204. The vessel 202 includes a distal end 206 and a proximal end 208. The outer diameter of the vessel 202 may range from about 152.4 mm to about 914.4 mm. The collection device 200 further includes an inlet port 210 extending from the proximal end 208 of the vessel 202. The inlet port 210 is in fluid communication with the chamber 204. The inlet port 210 may have an outer diameter ranging from about 12.7 mm to about 101.6 mm. Further, the collection device 200 includes an outlet port 212 extending from the proximal end 208 of the vessel 202. As shown in FIGS. 7 and 8, the outlet port 212 is in fluid communication with the chamber 204, and the outlet port 212 includes a porous material 214 positioned between the chamber 204 and the outlet port 212. The outer diameter of the outlet port may range from about 12.7 mm to about 50.8 mm.

As shown in FIGS. 5-9, the collection device 200 may further include a sampling tube 216 having a distal end 218 and a proximal end 220. The outer diameter of the sampling tube 216 may range from about 6.35 mm to about 25.4 mm. As shown in FIGS. 7 and 8, the proximal end 220 of the sampling tube 216 extends from the proximal end 208 of the vessel 202, and the distal end 218 of the sampling tube 216 extends into the chamber 204. The sampling tube 216 may be configured to remove a small sample of particles from the chamber 204 during a particle production run in which additional particles are being formed. In particular, the sampling tube 216 may include a sample thief that enables an operator to remove a small sample of particles without opening the chamber 204 or removing the sampling tube 216 from the rest of the collection device 200 during processing. This enables an operator to test a small sample of particles to ensure that the product is within specifications as the process continues to run. For example, particle size or residual solvent analysis may be performed on the sample. If the measured specifications do not match the desired specifications, the operating parameters of the particle formation process may be suitably adjusted to correct the situation before an entire batch of product with undesirable characteristics is created.

The porous material 214 positioned between the chamber 204 and the outlet port 212 may take a variety of forms. In one example, the porous material 214 is selected from the group consisting of a frit, a mesh, a cloth. As one specific example, the porous material 214 may comprise a high-efficiency particulate arrestance (HEPA) filter. An example HEPA filter may include a mat of randomly arranged fibers, the fibers composed of fiberglass and possessing diameters between about 0.5 micrometers and about 2.0 micrometers. In another example, the porous material 214 comprises a sintered filter having a distal end 222 and a proximal end 224. In such an example, the proximal end 224 of the sintered filter extends from the proximal end 208 of the vessel 202 and is coupled to the outlet port 212, and the distal end 222 of the sintered filter extends into the chamber 204. Such a sintered filter may include a porous stainless steel filter cartridge, as an example. Other porous materials are possible as well.

The inlet port 210 may include a coupling mechanism connects an outlet of a particle filtration system to the inlet port 210. In one example, the coupling mechanism comprises one or more sanitary fittings. In another example, the coupling mechanism comprises a threaded connection between the outlet of the particle filtration system to the inlet port 210. In yet another example, the coupling mechanism comprises one or more compression fittings. Other example coupling mechanisms are possible as well.

Figure 10:
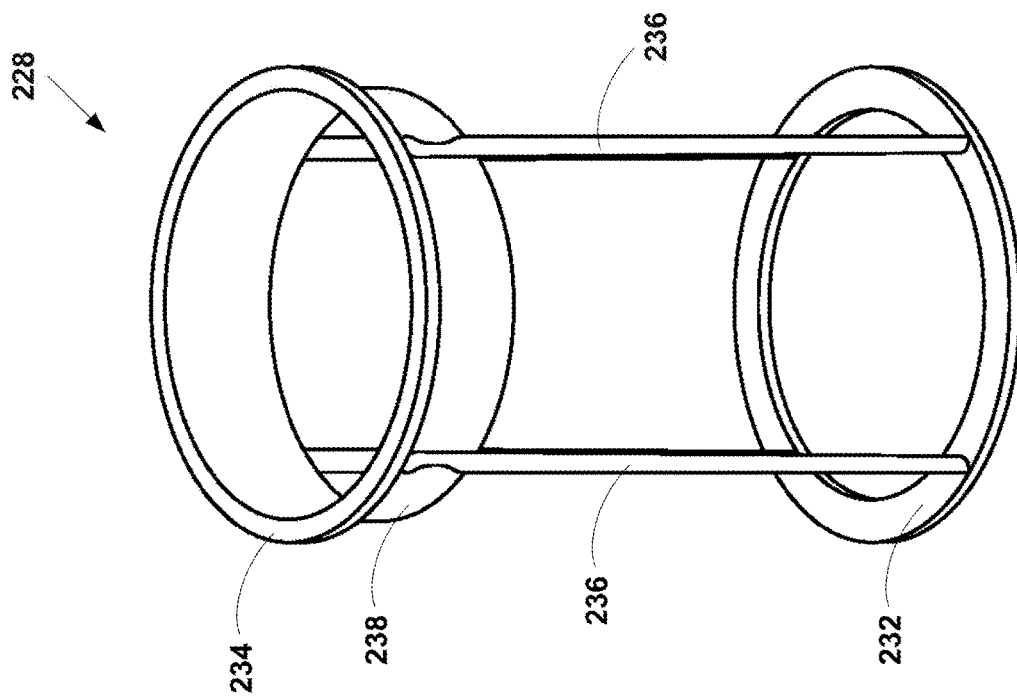
FIG. 10 illustrates a perspective view of a support frame, according to an example embodiment.
Figure 9:
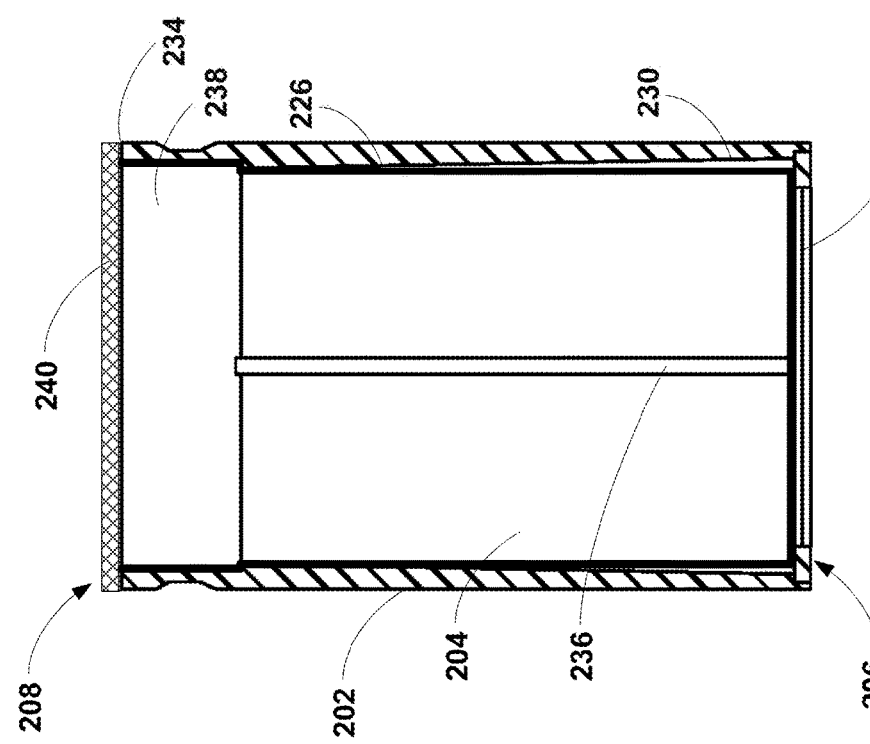
FIG. 9 illustrates another cross-section view of the particle collection device, according to an example embodiment.

Further, as shown in FIG. 9, the collection device 200 may further include a collection insert 226 positioned within the chamber 204 of the vessel 202, and a support frame 228 positioned between an interior wall 230 of the chamber 204 and the collection insert 226. The collection insert 226 may be a plastic bag, as an example. As shown in FIG. 10, the support frame 228 may include a distal ring 232, a proximal ring 234, one or more support legs 236 connecting the distal ring 232 to the proximal ring 234, and a gasket 238 positioned adjacent to the proximal ring 234. In one example, the gasket 238 may comprise a neoprene gasket. The vessel 202 may include a removable lid 240 that can be removed to access the collection insert 226 once particle collection is completed. In such an example, the collection insert 226 may be positioned within the chamber 204 of the vessel 202 such that top edge of the collection insert 226 folds over the top of the support frame 228 and is sealed between the gasket 238 and the removable lid 240 when the lid is in the closed position. Other arrangements are possible as well.

In one particular example method, a solution of 65 mg/ml of paclitaxel is prepared in acetone. The nozzle and a sonic probe are positioned in the pressurizable chamber approximately 8 mm apart. A stainless steel mesh filter with approximately 100 nm holes is attached to the pressurizable chamber to collect the precipitated paclitaxel nanoparticles. The supercritical carbon dioxide is placed in the pressurizable chamber of the manufacturing equipment and brought to approximately 1200 psi at about 37° C. and a flow rate of 18 kg per hour. The sonic probe is adjusted to an amplitude of 60% of maximum output at a frequency of 20 kHz. The acetone solution containing the paclitaxel is pumped through the nozzle at a flow rate of 2 mL/minute for approximately 60 minutes. The precipitated paclitaxel agglomerates and particles are then collected from the supercritical carbon dioxide as the mixture is pumped through the stainless steel mesh filter. The filter containing the nanoparticles of paclitaxel is opened and the resulting product is collected from the filter.

In one particular example method, a solution of 79.32 mg/ml of docetaxel is prepared in ethanol. The nozzle and a sonic probe are positioned in the pressurizable chamber approximately 9 mm apart. A stainless steel mesh filter with approximately 100 nm holes is attached to the pressurizable chamber to collect the precipitated docetaxel nanoparticles. The supercritical carbon dioxide is placed in the pressurizable chamber of the manufacturing equipment and brought to approximately 1200 psi at about 38° C. and a flow rate of 63 slpm (standard liters per minute). The sonic probe is adjusted to 60% of total output power at a frequency of 20 kHz. The ethanol solution containing the docetaxel is pumped through the nozzle at a flow rate of 2 mL/minute for approximately 95 minutes, until the drug solution is consumed. The precipitated docetaxel agglomerates and particles are then collected from the supercritical carbon dioxide as the mixture is pumped through the stainless steel mesh filter. The filter containing the nanoparticles of docetaxel is opened and the resulting product is collected from the filter.

Further, the system described above may be a component of a larger particle production system. Such a particle production system may include one or more nozzle assemblies such as those described above, a sonic energy source positioned adjacent to the orifice of each nozzle, one or more particle filtration systems in communication with one or more nozzle assemblies, and one or more particle collection devices in communication with the one or more particle filtration systems. In one example, the one or more particle filtration systems comprise a tandem particle filtration system including at least one high pressure harvesting filter system and at least one low pressure collection filter system in tandem and downstream to the harvesting filter. In such an example, the particle production system may include at least two particle harvesting filters, two particle collection filters and two collection devices.

In another aspect, the invention provides compound particles prepared by the method of any embodiment or combination of embodiments of the invention.

EXAMPLES

Materials and Methods

Raw paclitaxel and docetaxel were purchased from Phyton Biotech (British Columbia, Canada), lot number FP2-15004 and DT7-14025, respectively. Both were characterized in their raw form. The milling of both drugs was accomplished using a Deco-PBM-V-0.41 mill (Deco). The milling conditions for both compounds were as follows:
Ball size=5 mm
RPM=600
Processing time=60 min
Room temperature.

Preparation of Paclitaxel Particles

A solution of 65 mg/ml of paclitaxel was prepared in acetone. A BETE MicroWhirl® fog nozzle (BETE Fog Nozzle, Inc) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Paclitaxel nanoparticles produced had an average number-weighted mean size of 0.81 μm with an average standard deviation of 0.74 μm over three separate runs.

Preparation of Docetaxel Particles

A solution of 79.32 mg/ml of docetaxel was prepared in ethanol. The nozzle and a sonic probe were positioned in the pressurizable chamber approximately 9 mm (apart. A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

Docetaxel nanoparticles produced had an average number-weighted mean size of 0.82 μm with an average standard deviation of 0.66 μm over three separate ethanol runs.

Particle Size Analysis

Particle size was analyzed by both light obscuration and laser diffraction methods. An Particle Sizing Systems AccuSizer 780 SIS system was used for the light obscuration method and Shimadzu SALD-7101 was used for the laser diffraction method. Paclitaxel nanoparticles were analyzed using 0.10% (w/v) sodium dodecyl sulfate (SDS) in water as the dispersant. Docetaxel nanoparticles were analyzed using isopar G as the dispersant.

Paclitaxel suspensions were prepared by adding approximately 7 mL of filtered dispersant to a glass vial containing approximately 4 mg of paclitaxel particles. The vials were vortexed for approximately 10 seconds and then sonicated in a sonic bath approximately 1 minute. If the sample was already suspended, 1:1 solution of paclitaxel suspension to 0.1% SDS solution was made, vortexed for 10 seconds, and sonicated in the sonic bath for 1 minute.

Docetaxel suspensions were prepared by adding approximately 7 mL of filtered dispersant to a plastic vial containing approximately 4 mg of docetaxel particles. The vial was vortexed for approximately 10 seconds and then sonicated in a sonic bath for approximately 2 minutes. This suspension was used for laser diffraction analysis. Unused suspension was poured into a 125 mL particle-free plastic bottle, which was then filled to approximately 100 mL with filtered dispersant. The suspension was vortex for approximately 10 seconds and then sonicated in the sonic bath for approximately 2 minutes. This diluted suspension was used for light obscuration analysis.

A background test was first performed prior to analyzing particles on the AccuSizer 780 SIS. A new particle-free plastic bottle was filled with blank suspension solution by pumping from a reservoir, using a peristaltic pump, through a 0.22 μm Millipore filter and into the bottle.

A background analysis was run to ensure the particle/mL count was below 100 particles/mL. A small amount of paclitaxel suspension, 5-100 depending upon concentration of solution, was pipetted into the plastic bottle in place from the background test and was filled with ~100 mL dispersant and the analysis was started. Counts were monitored and paclitaxel solution added to reach and/or maintain 6000-8000 particle counts/mL during the entire analysis. Once the analysis was completed, the background data was removed and any measurement with less than four counts was removed.

To analyze particles on SALD-7101 using a batch cell, the analysis was started by choosing Manual Measurement. The refractive index was set as 1.5 to 1.7. The batch cell was filled with filtered dispersant just past the etched line. The blank measurement was ran. A small amount of API (paclitaxel or docetaxel) suspension was pipetted, generally <1 mL, depending upon concentration of solution as low as 100 into the batch cell as needed to achieve an acceptable absorbance between 0.15 and 0.2 absorbance units. The measurements were executed, and the resulting graph with the highest level of confidence was selected; background was automatically accounted for.

BET Analysis

A known mass between 200 and 300 mg of the analyte was added to a 30 mL sample tube. The loaded tube was then mounted to a Porous Materials Inc. SORPTOMETER®, model BET-202A. The automated test was then carried out using the BETWIN® software package and the surface area of each sample was subsequently calculated.

Bulk Density Analyte

Paclitaxel or docetaxel particle preparations were added to a 10 mL tared graduated cylinder through a plastic weigh funnel at room temperature. The mass of the drug was measured to a nearest 0.1 mg, the volume was determined to the nearest 0.1 mL and the density calculated.

Dissolution Studies

Paclitaxel

Approximately 50 mg of material (i.e.: raw paclitaxel, milled paclitaxel, or paclitaxel particles) were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a U(V/V) is spectrophotometer at 227 nm. Absorbance values of the samples were compared to those of standard solutions prepared in dissolution media to determine the amount of material dissolved.

Docetaxel

Approximately 50 mg of material (i.e.: raw docetaxel, milled docetaxel, or docetaxel particles) was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved.

Results

The BET surface area of particles produced using the above protocol and variations thereof (i.e.: modifying nozzles, filters, sonic energy sources, flow rates, etc.) ranged between 22 and 39 m$^2$/g. FIG. 1 shows exemplary particles produced using the methods of the invention.

Figure 2:
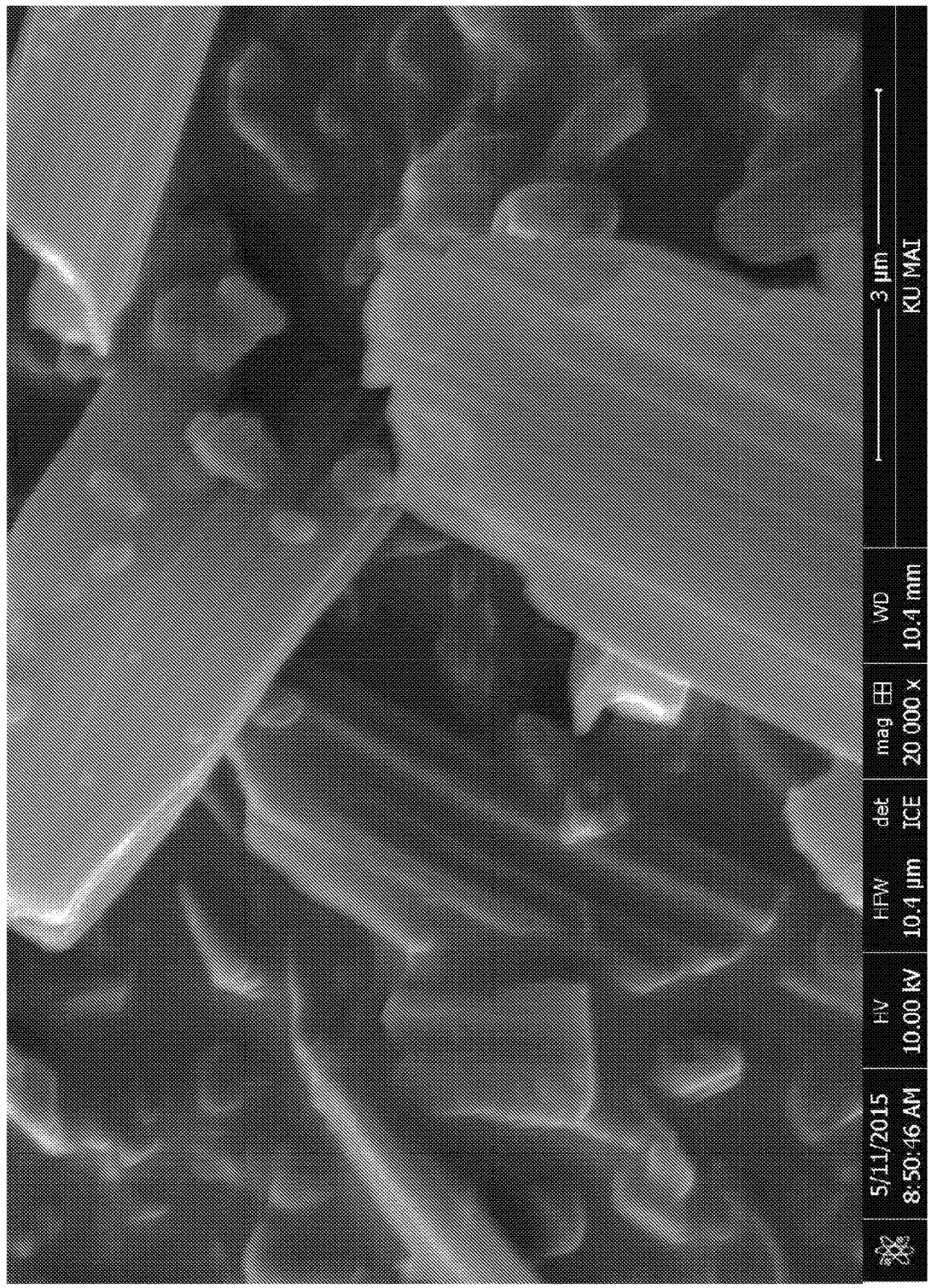
FIG. 2 is an electron micrograph of raw paclitaxel particles.

By comparison, the BET surface area of raw paclitaxel was measured at 7.25 m$^2$/g (FIG. 2), while paclitaxel particles made according to the methods of U.S. Pat. Nos. 5,833,891 and 5,874,029 ranged from 11.3 to 15.58 m$^2$/g. Exemplary particle sizes produced using the methods of the invention are shown in Table 1.

TABLE 1

| | Surface area m$^2$/g | Mean Size μm | | St Dev μm | |
|---|---|---|---|---|---|
| | | Number | Volume | Number | Volume |
| 1 | 38.52 | 0.848 | 1.600 | 0.667 | 0.587 |
| 2 | 33.82 | 0.754 | 0.988 | 0.536 | 0.486 |
| 3 | 35.90 | 0.777 | 1.259 | 0.483 | 0.554 |
| 4 | 31.70 | 0.736 | 0.953 | 0.470 | 0.466 |
| 5 | 32.59 | 0.675 | 0.843 | 0.290 | 0.381 |
| 6 | 38.22 | 0.666 | 0.649 | 0.344 | 0.325 |
| 7 | 30.02 | 0.670 | 0.588 | 0.339 | 0.315 |
| 8 | 31.16 | 0.672 | 0.862 | 0.217 | 0.459 |
| 9 | 23.90 | 0.857 | 1.560 | 0.494 | 0.541 |
| 10 | 22.27 | 0.857 | 1.560 | 0.494 | 0.541 |
| 11 | 26.19 | 0.861 | 1.561 | 0.465 | 0.546 |

Comparative studies on bulk density, SSA, and dissolution rates (carried out as noted above) for raw drug, milled drug particles, and drug particles produced by the methods of the present invention are provided in Tables 2 and 3 below. The full dissolution time course for the paclitaxel and docetaxel materials are provided in Tables 4 and 5, respectively.

TABLE 2

Compound: Paclitaxel

| Characteristic | Raw Material | Particles Batch 1 | Particles Batch 2 | Mean | Milled |
|---|---|---|---|---|---|
| Number Mean (um) | 1.16 | 0.83 | 0.67 | 0.75 | 0.89 |
| Volume Mean (um) | 1.29 | 1.42 | 0.57 | 1.00 | 1.35 |
| Bulk Density (g/cm$^3$) | 0.26 | 0.060 | 0.11 | 0.085 | 0.31 |
| Surface Area (m$^2$/g) | 10.4 | 35.6 | 39.8 | 37.7 | 15.0 |
| Dissolution (30 min) | 18% | 42% | 52% | 47% | 32% |

TABLE 3

Compound: Docetaxel

| Characteristic | Raw Material | Particles Batch 1 | Particles Batch II | Mean | Milled |
|---|---|---|---|---|---|
| Number Mean (um) | 1.58 | 0.92 | 0.80 | 0.86 | 1.11 |
| Volume Mean (um) | 5.05 | 4.88 | 4.03 | 4.46 | 3.73 |
| Bulk Density (g/cm$^3$) | 0.24 | 0.062 | 0.096 | 0.079 | 0.44 |
| Surface Area (m$^2$/g) | 15.9 | 43.0 | 45.4 | 44.2 | 15.2 |
| Dissolution (30 min) | 11% | 27% | 27% | 27% | 9% |

TABLE 4

Paclitaxel Dissolution time course

| Timepoint (minutes) | Paclitaxel Raw Material | Paclitaxel Particles | Milled Paclitaxel |
|---|---|---|---|
| 0 | 0.0% | 0.0% | 0.0% |
| 10 | 14.0% | 40.2% | 23.0% |
| 20 | 17.8% | 47.6% | 30.0% |
| 30 | 18.4% | 51.9% | 32.3% |
| 60 | 23.9% | 58.3% | 38.6% |
| 90 | 28.6% | 62.9% | 43.5% |

TABLE 5

Docetaxel Dissolution time course

| Timepoint (minutes) | Docetaxel Raw Material | Docetaxel Particles | Milled Docetaxel |
|---|---|---|---|
| 0 | 0.0% | 0.0% | 0.0% |
| 5 | 3.2% | 12.1% | 3.2% |
| 15 | 6.9% | 21.7% | 5.9% |
| 30 | 11.2% | 27.2% | 9.3% |
| 60 | 16.4% | 32.9% | 12.2% |
| 120 | 22.4% | 38.9% | 13.6% |
| 225 | 26.8% | 43.1% | 16.0% |

We claim:

1. A composition, comprising particles including at least 95% by weight of paclitaxel, or a pharmaceutically acceptable salt thereof, wherein the particles have
    (a) a specific surface area (SSA) of between 18 m$^2$/g and about 40 m$^2$/g,
    (b) a mean bulk density between about 0.050 g/cm$^3$ and about 0.12 g/cm$^3$, and
    (c) a mean particle size of between about 0.4 μm to about 3 μm; and
    wherein the particles include both agglomerated particles and non-agglomerated particles.

2. The composition of claim 1, wherein the particles have a SSA of between about 20 m$^2$/g and about 40 m$^2$/g.

3. The composition of claim 1, wherein the particles have a mean particle size of between about 0.4 μm to about 1.2 μm.

4. The composition of claim 1, wherein the particles comprise at least 98% by weight of paclitaxel, or a pharmaceutically acceptable salt thereof.

5. The composition of claim 3, wherein the particles comprise at least 98% by weight of paclitaxel, or a pharmaceutically acceptable salt thereof.

6. The composition of claim 1, wherein the composition comprises a suspension further comprising a pharmaceutically acceptable aqueous carrier.

7. The composition of claim 3, wherein the composition comprises a suspension further comprising a pharmaceutically acceptable aqueous carrier.

8. The composition of claim 4, wherein the composition comprises a suspension further comprising a pharmaceutically acceptable aqueous carrier.

9. The composition of claim 5, wherein the composition comprises a suspension further comprising a pharmaceutically acceptable aqueous carrier.

10. A composition, comprising particles including at least 95% by weight of docetaxel, or a pharmaceutically acceptable salt thereof, wherein the particles have
    (a) a specific surface area (SSA) of between 18 m$^2$/g and about 50 m$^2$/g,
    (b) a mean bulk density between about 0.050 g/cm$^3$ and about 0.12 g/cm$^3$, and
    (c) a mean particle size of between about 0.4 μm to about 3 μm; and
    wherein the particles include both agglomerated particles and non-agglomerated particles.

11. The composition of claim 10, wherein the particles have a SSA of between about 20 m$^2$/g and about 50 m$^2$/g.

12. The composition of claim 10, wherein the particles have a mean particle size of between about 0.4 μm to about 1.2 μm.

13. The composition of claim 10, wherein the particles comprise at least 98% by weight of paclitaxel, or a pharmaceutically acceptable salt thereof.

14. The composition of claim 12, wherein the particles comprise at least 98% by weight of paclitaxel, or a pharmaceutically acceptable salt thereof.

15. The composition of claim 10, wherein the composition comprises a suspension further comprising a pharmaceutically acceptable aqueous carrier.

16. The composition of claim 12, wherein the composition comprises a suspension further comprising a pharmaceutically acceptable aqueous carrier.

17. The composition of claim 13, wherein the composition comprises a suspension further comprising a pharmaceutically acceptable aqueous carrier.

18. The composition of claim 14, wherein the composition comprises a suspension further comprising a pharmaceutically acceptable aqueous carrier.

* * * * *